(12) United States Patent
Kaufmann et al.

(10) Patent No.: US 7,985,250 B2
(45) Date of Patent: Jul. 26, 2011

(54) INSERTION SYSTEM FOR STENTS, COMPRISING TENSION-COMPRESSION KINEMATICS

(75) Inventors: Ralf Kaufmann, Rangendingen (DE); Stefan Derkvist, Hechingen (DE); Berthold Hauser, Burladingen (DE)

(73) Assignee: JOTEC GmbH, Hechingen (DE)

( * ) Notice: Subject to any disclaimer, the term of this patent is extended or adjusted under 35 U.S.C. 154(b) by 79 days.

(21) Appl. No.: 12/177,915

(22) Filed: Jul. 23, 2008

(65) Prior Publication Data

US 2009/0030496 A1 Jan. 29, 2009

Related U.S. Application Data

(63) Continuation of application No. PCT/EP2007/000403, filed on Jan. 18, 2007.

(30) Foreign Application Priority Data

Jan. 25, 2006 (DE) .......................... 10 2006 004 123

(51) Int. Cl.
*A61F 2/06* (2006.01)
(52) U.S. Cl. .................................................... 623/1.11
(58) Field of Classification Search .............. 623/1.11, 623/1.12, 1.23; 606/108, 194, 200, 191, 606/198; 604/95.01, 95.03, 95.04, 523–527, 604/530, 57–64; 83/435.18, 437.5, 613–641; 74/110, 505, 506, 500.5, 501.5 R; 254/389, 254/390
See application file for complete search history.

(56) References Cited

U.S. PATENT DOCUMENTS

| 4,154,239 | A | * | 5/1979 | Turley ............................. 604/61 |
| 4,411,653 | A | | 10/1983 | Razi |
| 4,444,560 | A | | 4/1984 | Jacklich |
| 4,753,322 | A | * | 6/1988 | Yasuda .......................... 187/254 |
| 4,820,287 | A | | 4/1989 | Leonard |
| 5,026,377 | A | | 6/1991 | Burton et al. |
| 5,667,476 | A | * | 9/1997 | Frassica et al. ............... 600/149 |
| 5,707,376 | A | | 1/1998 | Kavteladze et al. |
| 5,944,727 | A | | 8/1999 | Ahari et al. |
| 6,136,006 | A | | 10/2000 | Johnson et al. |
| 6,402,760 | B1 | | 6/2002 | Fedida |

(Continued)

FOREIGN PATENT DOCUMENTS

DE 698 06 550 T2 11/2002

(Continued)

OTHER PUBLICATIONS

European Search Report for European Patent Application No. EP09169903 dated Dec. 23, 2009.

*Primary Examiner* — Anhtuan T Nguyen
*Assistant Examiner* — Katherine M Shi
(74) *Attorney, Agent, or Firm* — Knobbe Martens Olson & Bear LLP

(57) ABSTRACT

The present invention relates to a device for inserting a self-expanding stent into a body vessel. The device comprises a tube, a pushing element and a grip having a housing via which the pushing element is secured on the grip. Further, the device comprises a stent carrier and a moveable element, the latter of which is guided in the housing of the grip and is coupled to the pushing element. Moving the movable element in the proximal direction effects a movement of the pushing element in the distal direction and a movement of the tube in the proximal direction.

15 Claims, 18 Drawing Sheets

U.S. PATENT DOCUMENTS

| | | |
|---|---|---|
| 6,514,261 B1 | 2/2003 | Randall et al. |
| 7,105,016 B2 | 9/2006 | Shiu et al. |
| 2003/0191516 A1 | 10/2003 | Weldon et al. |
| 2004/0138734 A1 | 7/2004 | Chobotov |
| 2004/0176682 A1 | 9/2004 | Murphy |
| 2006/0184238 A1 | 8/2006 | Kaufmann et al. |
| 2008/0082154 A1* | 4/2008 | Tseng et al. ............ 623/1.11 |

FOREIGN PATENT DOCUMENTS

| | | |
|---|---|---|
| DE | 103 35 649 A1 | 2/2005 |
| DE | 10 2004 023 559 | 9/2005 |
| DE | 102005059261 | 6/2007 |
| EP | 1 078 611 | 2/2001 |
| EP | 1 210 959 | 6/2002 |
| EP | 1391181 | 2/2004 |
| EP | 1415616 | 5/2004 |
| EP | 1 440 671 A2 | 7/2004 |
| EP | 1440672 | 7/2004 |
| EP | 1 117 341 | 12/2004 |
| EP | 1894545 | 3/2008 |
| EP | 1923024 | 5/2008 |
| EP | 1943988 | 7/2008 |
| JP | 58-086175 A | 5/1983 |
| JP | 62-243552 A | 10/1987 |
| JP | 10-511016 A | 10/1998 |
| WO | WO 2005/067819 | 7/2005 |

* cited by examiner

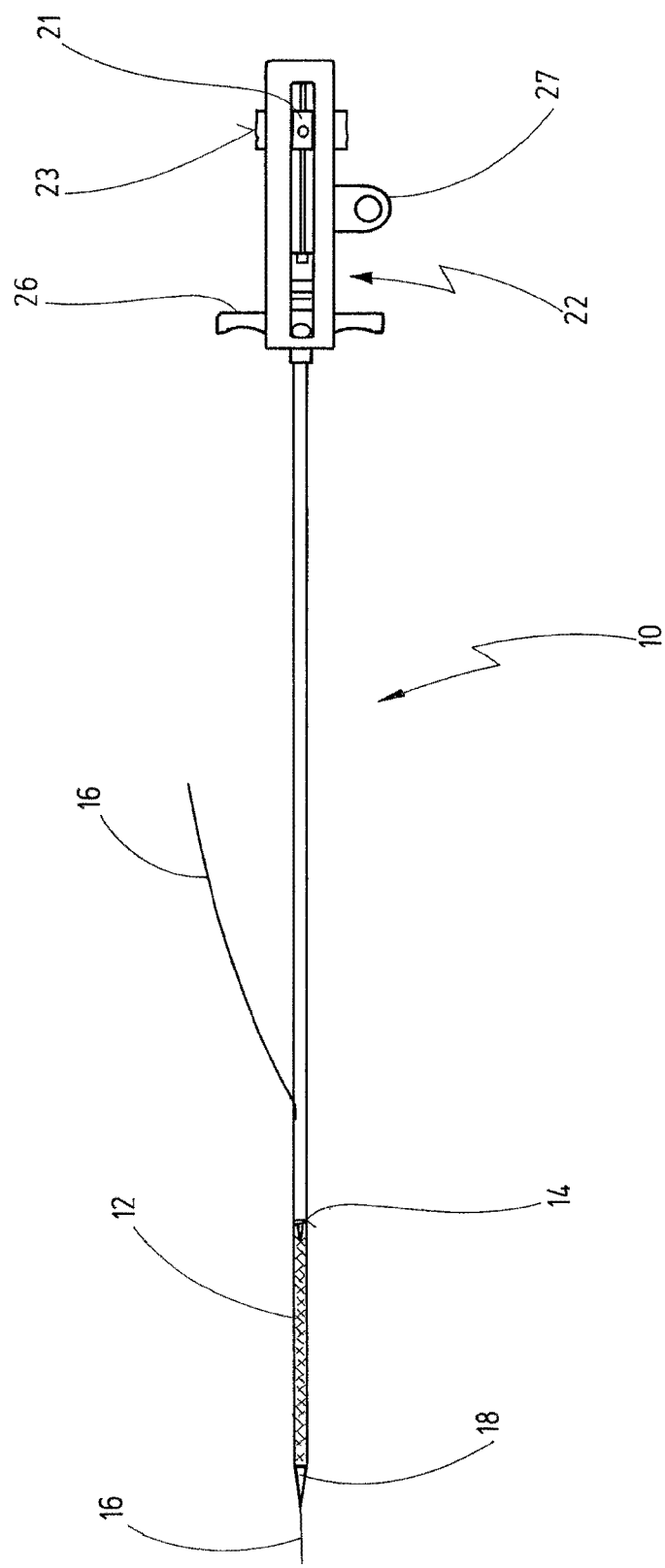

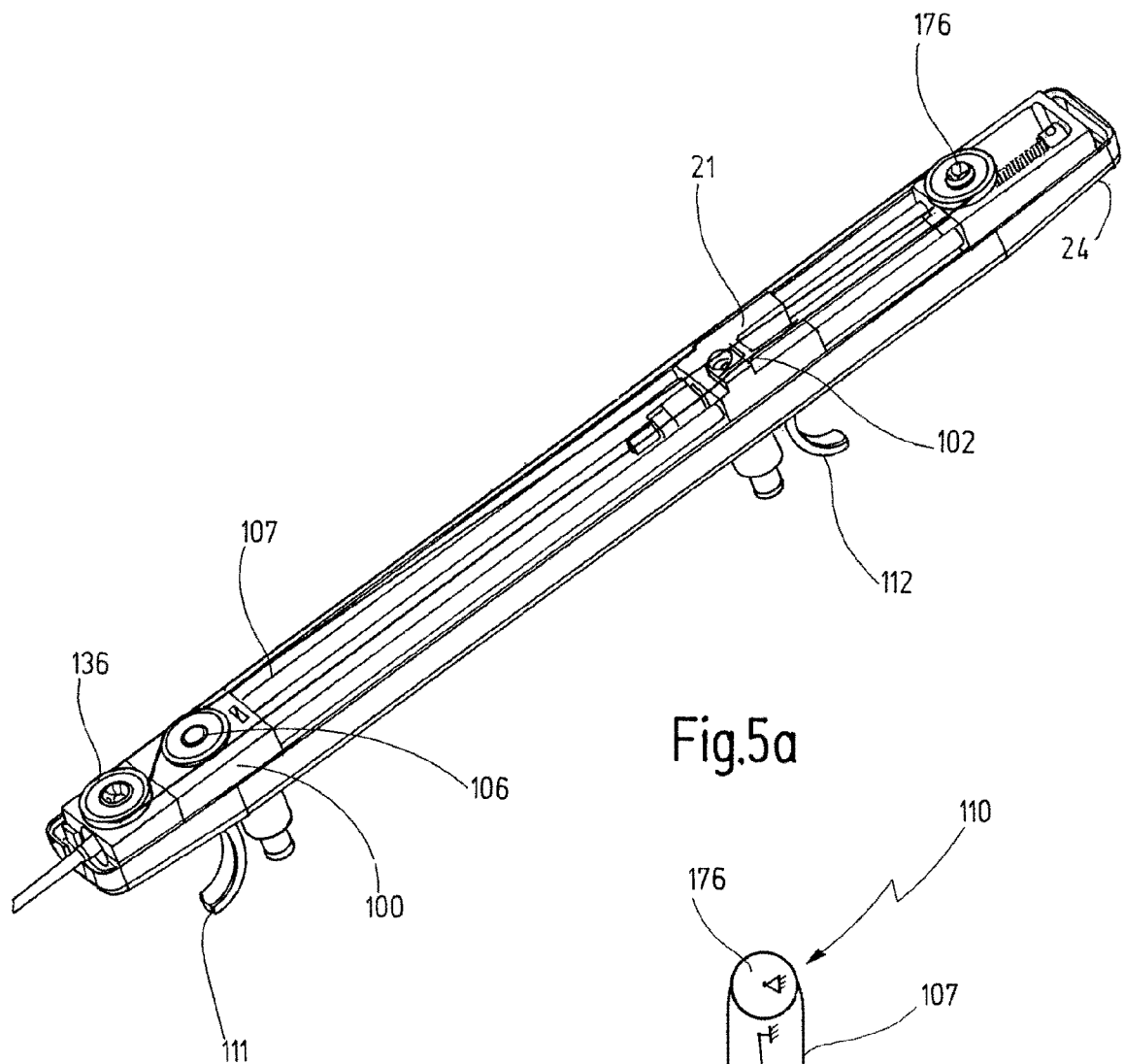
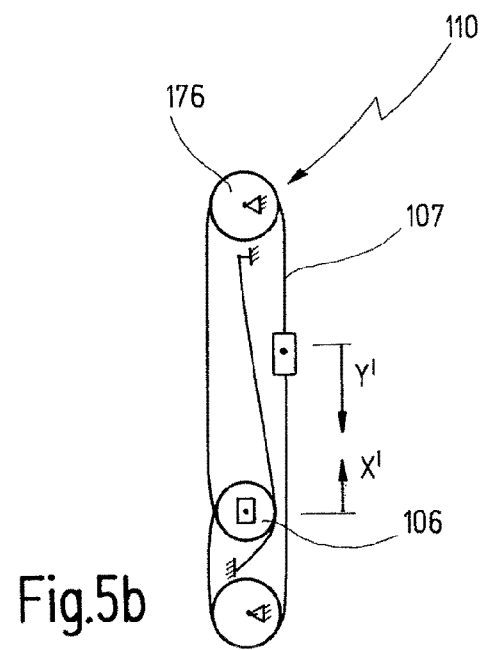

INSERTION SYSTEM FOR STENTS, COMPRISING TENSION-COMPRESSION KINEMATICS

CROSS REFERENCE TO RELATED APPLICATIONS

This is a continuation application of International Patent Application PCT/EP2007/000403, filed Jan. 18, 2007, designating the United States and published in German as WO 2007/085373 A1, which claims priority of German application number DE 10 2006 004 123.2, filed Jan. 25, 2006, whose contents are incorporated herein by reference.

BACKGROUND OF THE INVENTION

1. Field of the Invention

The present invention relates to a device for inserting a self-expanding stent into a body vessel, with a tube which, in a distal portion, keeps the stent radially compressed, with a pushing element which is guided in the tube and has a proximal end and a distal end, also with a grip that comprises a housing via which the pushing element is secured displaceably on the grip, and also with a stent carrier which is guided in the pushing element and which has a tip which is mounted fixedly on the device via the grip.

2. Related Prior Art

Such devices for insertion of self-expanding stents are known from the prior art. Such insertion systems are used to implant endovascular stents into blood vessels that have been damaged, for example as a result of diseases or the like, or that have had their lumen occluded, as a consequence of which the function of the vessels is greatly impaired. In the prior art, various implantable stent devices are known which, after they have been implanted, keep blood vessels, for example arteries, open. Such stents generally have a tubular body which is inserted into the vessel and is fixed at the relevant location in order to keep the lumen of the vessel open.

Thus, the prior art includes stent grafts, for example, which have a wire framework made of a self-expanding material, and the wire framework can additionally be connected to a tube made of textile.

For implantation, the stent is radially compressed, such that its cross-sectional surface area can be considerably reduced and it can easily be inserted into the vessel. On account of the resiliency of the metal framework, the stent expands back to its original shape and in so doing stretches its jacket surface, which wedges itself internally in the blood vessel.

For implantation, the stents are folded up radially and, with the aid of catheters advanced through the lumen, are then introduced into the blood vessel and placed in the correct position in the vessel. The correct position of the stent can be monitored using X-ray markers, for example. To ensure that the stents remain in the comprised state during their positioning, they are arranged in a sleeve or in a sheath-like tube which, by virtue of its properties, presses the stent radially inwards. This so-called withdrawal sleeve is pulled back after the stent has been positioned in the vessel, in which process the stent is held axially by an abutment element, which is also designated as a pusher. The pusher lies in contact with the stent and holds the latter in its axial position, while the withdrawal sleeve also surrounding the pusher is detached from the stent, which is thus able to expand and wedge itself in the blood vessel.

A very wide variety of stents are used depending on the type of application. The present invention is concerned with the application of what are called braided stents. These are metal stents that are produced by what is called a plain weaving technique. They are composed of a hollow body, which can stretch in the longitudinal direction and whose jacket is a braid made up of a multiplicity of filament-like elements which, in the expanded state of the braided stent, intersect a plane, perpendicular to the longitudinal direction, at a braid angle. A braided stent undergoes a considerable change in length when stretched, this change in length being all the greater the greater the original diameter and the smaller the original braid angle.

For implantation, a braided stent of this type is stored in an elongate configuration in an insertion system or applicator, the latter being introduced percutaneously into the body at a suitable location and being guided through a lumen as far as the vessel where the stent is to be released.

In stents that experience no change or only a very slight change in length when released, the position of the implantable stent can be easily verified, for example using X-ray markers.

In braided (metal) stents, however, a problem that arises is that they grow much shorter when released. The ratio I/L of the stent length I in the loaded state to the free stent length L is dependent on the diameters d in the insertion system and D in the unloaded state and also on the braid angle $\alpha$:

$$I/L = (D^2 - d^2 \cdot \cos^2 \alpha)^{1/2} / (D \cdot \sin \alpha).$$

For example, when a stent with a length L=40 mm, a diameter D=6 mm and a braid angle $\alpha$=40° is compressed to a diameter d=1.5 mm in an insertion system, it becomes longer by a factor I/L=1.53. Accordingly, it therefore has a length of 61.2 mm in the insertion system. In a stent with a functional zone, e.g. with a braid angle of $\alpha$=10°, as is described in patent application DE 103 35 649, for example, the lengthening in the insertion system can even be by a factor I/L=4 to 6.

Braided stents are therefore extremely extensible and, in their elongated state, they as it were store mass which, upon contraction of the stent, ensures a compact and stiff functional area, as is explained in detail in aforementioned DE 103 35 649.

Stents in which this kind of shortening upon release has to be taken into account can no longer be released with precision using the currently existing insertion systems.

For example, the prior art includes insertion systems for stents that experience extreme shortening upon release. In the insertion systems known in the prior art, the problem of shortening is solved by limiting the distal travel of the tip to a few millimeters relative to the sleeve tube. In such insertion systems, the insertion system has to be carefully pulled back at the same time as the stent is being released. This positioning, with millimeter precision, of a braided stent that shortens considerably requires practice on the part of the user and a great deal of experience. The precision and handling characteristics of this system are adapted to the treatment of long peripheral vascular lesions (greater than 3 cm) using suitably long braided stents. For positioning with millimeter precision in short areas of stenosis, as may occur in the internal carotid artery for example, such systems do not afford the required precision.

SUMMARY OF THE INVENTION

Against this background, an object of the present invention is to make available an insertion system which, by simple structural means, allows braided stents to be released with improved positioning accuracy, in particular in short areas of stenosis.

In the device mentioned at the outset, this object is achieved, according to the invention, by the fact that a movable element, which is guided in the housing of the grip, is coupled to the proximal end of the pushing element in such a way that, by a movement of the movable element in the proximal direction, the pushing element can at the same time be guided in the distal direction, and the tube can be guided in the proximal direction.

The inventors of the present application have in fact found that, by coupling the movement of the tube or sleeve tube to the pushing element or pusher, it is ensured that the user can achieve extremely precise positioning by a simple maneuver. The insertion system according to the invention thus makes it possible for braided stents that undergo considerable shortening to be positioned with millimeter precision even by less experienced and practiced users.

The term "distal" in the present context designates the direction/end of the device or parts of the device leading away from the user (i.e. in the direction of the tip of the stent carrier); the term "proximal" designates the direction/end of the device or parts of the device leading toward the user.

It will be appreciated that the proximal end of the pushing element located in the housing can be formed integrally with the other portions of the pushing element that also extend partly outside the housing, or it can be composed of one or more separate elements which, in the assembled insertion system, form one unit with the other component parts of the pushing element.

The stent can therefore be released continuously by the tube being visibly pulled back and, at the same time, by the pushing element or pusher being pressed in the opposite direction in a manner not visible to the user. This is achieved by the coupling, provided in the device according to the invention, between movable element and pushing element. Thus, for example, by means of tube being pulled back in the proximal direction, the movable element can likewise be guided in a proximal direction. By virtue of the coupling to the proximal end of the pushing element, the pushing element is then simultaneously moved in the distal direction, as a result of which the radially compressed and thus greatly "lengthened" stent can be released into the relatively short vessel placement area.

At the same time, the grip of the device and, with it, the tip of the stent carrier remain fixed in position, that is to say relative to the lesion, throughout the entire stent release procedure. The stent carrier can have X-ray markers.

At the start of the release of the stent, the tip of the stent carrier first comes free as a result of the relative movement between tube and pushing element, and the distal end of the stent also emerges from the outer sleeve and expands, i.e. comes free from the tip. The stent is released by further pulling back of the sleeve tube and by the mechanically generated opposite movement of the pushing element.

In a further embodiment, the movable element is coupled to the pushing element via a deflecting gear provided in the grip, in particular via a cable pulley deflecting gear. "Deflecting gear" is intended to signify any component/components with which a movement in one direction is simultaneously converted into a movement in another direction.

This measure has the advantage that, by integrating a deflecting gear into the grip, a component is made available which is easy to use and with which stents, as described above, can be easily and precisely released.

The deflecting gear has the effect that a displacement of the movable element in the proximal direction results in the movement of the pushing element in the distal direction.

In a further embodiment, the movable element is coupled to the proximal end of the pushing element lying in the housing via a deflecting gear provided in the grip.

In yet another embodiment, the proximal end of the pushing element has a flange via which the movable element is coupled to the pushing element.

This measure has the advantage that the flange affords a suitable surface on which, for example, elements of the deflecting gear can be secured. Depending on the design of the deflecting gear, the tensioning thread can be secured with one of its ends on the flange and/or can be guided via a deflection element provided on the flange.

According to another embodiment, the flange provided in the grip is dimensioned such that elements of the flange can be gripped from outside the housing. Flange and pushing element preferably form one structural unit.

This measure has the advantage that the pushing element can be guided, independently of the movement of the movable element, via the elements of the flange that protrude outside the grip. For this purpose, all that has to be done is to take hold of the outer elements of the flange that protrude from the housing of the grip. It will be understood that further gripping elements can be provided on the flange, in addition to the ends protruding from the housing. For example, the elements of the flange can be designed such that the flange, and with it indirectly also the pushing element, can be gripped as firmly as possible and in a manner secure against slipping. For this purpose, the elements of the flange can, for example, have a "grooved" or other kind of roughened surface to prevent slipping of the grip on the flange and to make manual guiding of the pushing element easier.

In one embodiment of the device according to the invention, it is preferable if a pulling grip, which is coupled to the tube, is also provided in the housing.

This embodiment has the advantage that the movable element can be displaced in the proximal direction initially by the movement of the pulling grip, which is coupled to the tube, or by the structural arrangement of the movable element in the grip, which movable element is arranged in series with the pulling grip, or is arranged downstream of the pulling grip, as seen in the proximal direction. By virtue of the coupling, for example via a deflecting gear, the movable element, thereby set in motion, in turn causes the movement of the pushing element in the distal direction.

The stent is released, on the one hand, by the pulling back of the tube that compresses the stent, and, on the other hand, by the active opposing action by the pushing element.

The pushing element is arranged in the housing of the grip in such a way that the movable element and the pulling grip are guided along the pushing element, or the pushing element is arranged to be displaceable in the distal direction at least partially through the movable element and the pulling grip.

In one embodiment of the insertion system according to the invention, it is preferable if the deflecting gear has a tensioning thread which is secured with one of its ends on the distal part of the housing, is further guided to the pushing element via a first deflection element provided on the movable element and via a second deflection element provided in the distal end of the housing, and is secured with a second end on the pushing element.

This embodiment has the advantage that a transmission ratio X/Y of 0.5 can be achieved with the deflecting gear, where X is the path of the movable element relative to the path Y of the pushing element.

In another embodiment of the device according to the invention, it is preferable if the deflecting gear has a tensioning thread which is secured with one of its ends on the movable element, is further guided to the pushing element via a deflection element provided on the distal end of the housing, and is secured with its second end on the pushing element.

In this embodiment, a transmission ratio X/Y of 1 can advantageously be achieved.

In another embodiment, it is preferable if the deflecting gear has a tensioning thread which is secured with one of its ends on the movable element, is further guided to the pushing element via a first deflection element provided on the distal end of the housing, is guided to the distal end of the housing via a second deflection element provided on the pushing element, and is secured with its second end on the distal end of the housing.

This embodiment has the advantage that a transmission ratio X/Y of 2 can be achieved.

As has been set out above, the different configurations of the deflecting gear can be used to generate different transmission ratios, which can be selected for the specific application, depending on the stent that is to be inserted, on the vessel length, or on the experience of the user.

The choice of embodiment will be made depending in particular on the value of the factor I/L of the stent or of individual stent zones (stent length I in the loaded state in relation to the free stent length L).

However, it is also possible, for example, to vary the initial return travel Z of the tube and to adapt it to the existing stent diameter and stent angle. In this way, for example, irrational numbers are also permitted as total transmission ratios $(Z+X)/Y \geqq 0.5$ between the return travel of the tube and the forward movement of the pushing element. The same effect is provided by a tensioning thread, loosened by the length L, and the combination of the structural elements.

It will be understood that the "tensioning thread" can be any filament-like element which, regardless of its nature or material, is able to provide the above-described features necessary for a deflecting gear. The tensioning thread must therefore have a high modulus of elasticity with good flexibility and low friction. For example, a woven textile can be used. The same applies to the deflection elements. These can, for example, be designed as small pulleys via which the tensioning thread is guided. There are also various options available for securing the ends of the tensioning thread, for example hook-shaped or eyelet-shaped elements, without any limitation to these being implied.

In a further embodiment, the device has another gear which works as an opposing gear of the deflecting gear.

This embodiment is advantageous in particular if the user wants to release the stent by pushing together the movable element and the flange. The opposing gear ensures that the tensioning thread cannot come loose, and that the intended gear transmission ratio between pulling grip and movable element is not abolished. Deflecting gear and opposing gear have the same gear transmission ratio. When the tensioning thread of the deflecting gear is subjected to compression and comes loose, the opposing gear is tensioned, and vice versa. In this way, the gear transmission ratio between pulling grip and movable element is maintained, irrespective of which element or which combination of elements is actuated by the user.

In other embodiments of the insertion system according to the invention or of the device according to the invention, it is preferable if the grip also has a gripping element mounted fixedly on the housing.

This measure has the advantage that the gripping element permits a secure hold of the grip or of the housing and thus also of the entire device. Accordingly, the gripping element can be designed, for example, in the form of a finger hole or thumb hole into which the user simply has to introduce an appropriate finger. The user's hand can then at the same time be engaged around the grip. The insertion system can be easily actuated using one hand. For this purpose, the user fits his thumb into the gripping element, as a result of which he acquires a hold of the entire grip of the insertion system. The gripping element ensures that the grip is fixed in the user's hand. If the stent is to be released after insertion into the corresponding vessel, the user can, for example, place his index finger and/or middle finger on the pulling grip and guide the latter in a proximal direction, as a result of which the stent, as described above, is released continuously.

In another embodiment of the device according to the invention, the starting distance between the pulling grip and the movable element is $\geqq 0$ mm ("greater than or equal to zero").

"Starting distance" in this context means the distance between pulling grip and movable element after the device has been inserted into a vessel and, therefore, at the start of the release mechanism.

In another embodiment of the device according to the invention, the movable element is designed as a tensioning element, in particular as a flange-shaped tensioning element, which is also coupled to the tube.

This embodiment permits a technically simple variant of the device according to the invention since, by pulling back the movable element or tensioning element, the sleeve is simultaneously pulled back from the stent, that is to say moved in the proximal direction, and the pushing element is also moved in the distal direction, as a result of which the stent can be released by a further action of force.

The design of the movable element as a flange has the effect that, as in the design of the proximal end of the pushing part as flange, a suitable surface is made available on which, for example, elements of the deflecting gear can be secured. Depending on the configuration of the deflecting gear, the tensioning thread can, for example, be secured with one of its ends on the flange and/or can be guided via a deflection element provided on the flange.

In a further development of the embodiment, it is preferable if the deflecting gear has a tensioning thread which is secured with one of its ends on the distal part of the housing, is further guided via a first deflection element provided on the tensioning element and via a second deflection element provided in the distal end of the housing to a deflection element provided on the proximal end of the housing, and is then guided, via a means provided on the proximal end of the pushing element for fixing the tensioning thread at the proximal end of the pushing element, back round the deflection element and is secured with its second end on the proximal end of the housing.

This embodiment has the advantage that a transmission ratio X/Y of 0.5 can be achieved with the deflecting gear, where X is the path of the movable element or tensioning element relative to the path Y of the pushing element.

In another development of the embodiment, it is preferable if the deflecting gear has a tensioning thread which is guided via a deflection element provided on the distal end of the housing, via a first means provided on the tensioning element for fixing the tensioning thread on the tensioning element, via a deflection element provided on the proximal end of the housing, and via a second means provided on the proximal end of the pushing element for fixing the tensioning thread on the proximal end of the pushing element.

In this development of the embodiment, a transmission ratio X/Y of 1 can advantageously be achieved.

In yet another development of the embodiment, it is preferable if the deflecting gear has a tensioning thread which is secured with one of its ends on the distal end of the housing and is guided via a deflection element provided on the proximal end of the pushing element, via a deflection element provided on the distal end of the housing, via a first means provided on the tensioning element for fixing the tensioning thread on the tensioning element, and via a deflection element provided on the proximal end of the housing, and from there back to the deflection element, and is secured with its second end on the proximal end of the housing.

With this development of the embodiment, a transmission ratio X/Y of 2 can be achieved.

"Deflection element" is understood as any structural element that is able to convert the movement or force produced by the tensioning thread in one direction. For example, deflection elements in the form of fixed or movable pulleys are preferred.

"Means for fixing the tensioning thread" on the proximal end of the pushing element or on the tensioning element are understood as any measure by which the tensioning thread is fixed on the pushing element or tensioning element in such a way that, when the tensioning element/pushing element is moved, the tensioning thread is entrained by virtue of its being fixed via the means provided. The "free" portions of the tensioning thread, that is to say those not fixed by the means, can then run via the deflection elements. Such "means for fixing" can, for example, be clamp elements. The tensioning thread, however, can also be fixed by other technical methods to the tensioning element/pushing element, for example by adhesive bonding, welding or the like.

In the developments described above, it is preferable if the tensioning element and/or the pushing element have elements that can be gripped from outside the housing. This measure has the advantage that the pushing element and the movable element/tensioning element can be actuated via the elements protruding outside the housing of the grip. Here too, it will be understood that in addition to the elements protruding from the housing, additional gripping elements can be provided. By designing gripping elements in the form of a "trigger", for example, the movable element and/or the pushing element can easily be set in motion by the user actuating the trigger with a finger.

In another embodiment, it is preferable if the device further comprises a stop element which is displaceable between the movable element and the pushing element.

This measure has the advantage that it prevents the movable element from initially abutting directly against the pushing element. This in turn ensures that a sufficient part of the proximal end of the stent remains lying in the tube and fixed on the pushing element.

The stop element is arranged in series with the pulling grip and the movable element. The movement of the pulling grip thus initially sets the movable element in motion, and the movable element can also be displaced in the proximal direction directly by movement of the pulling grip. The movable element then abuts, either directly or in the course of its movement, against the stop element, which is entrained by the movement of the movable element in the proximal direction. By means of the coupling of the movable element to the pushing element, the latter, as has been described above, is guided in the distal direction, as a result of which it is moved counter to the movable element and the stop element.

Depending on the design of the deflecting gear, the pushing element and the stop element, entrained by the movement of the movable element, abut against each other after a defined length of travel.

The stop element can also be mounted removably directly on the movable element.

In another embodiment, the stop element can also be mounted in or on the grip not as a displaceable element, but as a removable element.

By virtue of the stop element, it is advantageously possible to pull the stent back completely into the insertion system, should it be necessary to do so in a given situation. It is even possible to pull the stent back into the tube in the position in which the movable element abuts against the pushing element via the stop element. For this purpose, the pushing element can be pulled in the proximal direction, for example via its flange, which can be gripped from outside of the housing. By means of the movement of the pushing element in the proximal direction, the movable element is in turn moved (back) in the distal direction, as a result of which the pulling grip and the tube coupled to the pulling grip are moved in the distal direction. In this way, the stent can be guided back into the insertion system.

According to another embodiment, the stop element is mounted removably between movable element and pushing element.

This measure has the advantage that the stent can then be finally released, for which purpose the stop element between the movable element and the pushing element can be simply removed, for example pulled out. In this way, in a subsequent step, the movable element can then be moved fully in the distal direction and be brought into direct contact with the pushing element, as a result of which, finally, the proximal end of the stent is fully released.

In the device according to the invention, the pushing element is preferably guided through the stop element, the movable element and the pulling grip. All the elements, that is to say the pushing element, the movable element, the stop element and the pulling grip, can be displaced relative to one another, or are mounted displaceably relative to one another, and, as has been described, the pushing element is guided displaceably through the other elements.

Further advantages and features will become evident from the following description and from the attached drawings.

BRIEF DESCRIPTION OF THE DRAWINGS

Illustrative embodiments of the invention are explained in more detail in the following description and are depicted in the drawing, in which:

FIG. 1 shows the overall view of an insertion system with loaded stent, which view is not intended to be true to scale;

FIG. 5a shows a schematic, perspective view (not true to scale) of another embodiment of the proximal (grip) portion of the insertion system according to the invention, in the unactuated state and therefore before release of the stent (not shown), the housing being shown here only in part so as to better illustrate the interior of the housing;

FIG. 5b shows a schematic view of the course of the tensioning thread;

DESCRIPTION OF PREFERRED EMBODIMENTS

Figure 2A:
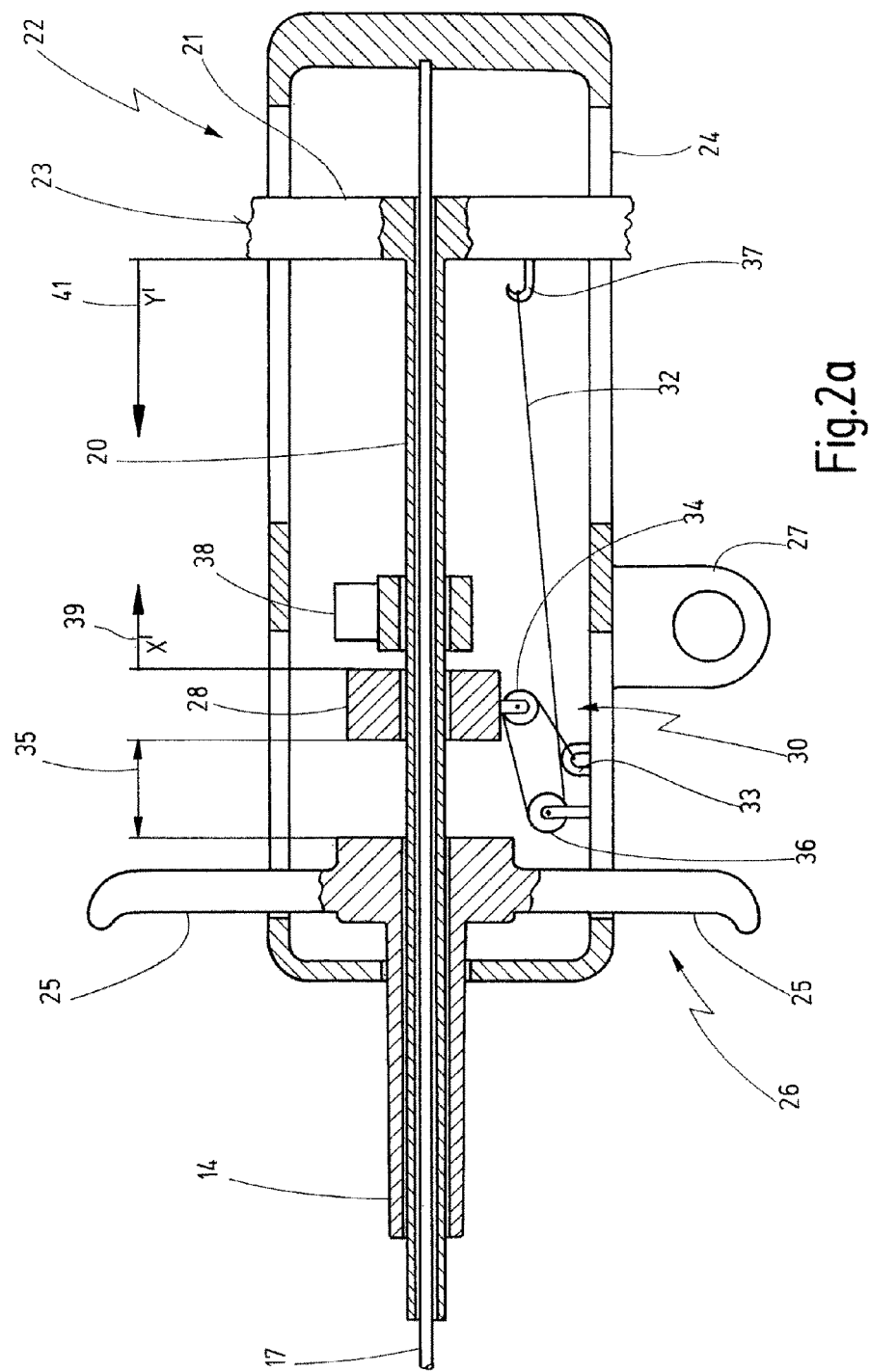
FIG. 2a shows an enlarged, schematic longitudinal section (not true to scale) through the proximal portion of the insertion system from FIG. 1, in a first illustrative embodiment.

An insertion system, shown schematically in FIG. 1 and designated overall by reference number 10, can be used to insert a stent or braided stent 12 into a blood vessel.

The stent 12 can be a self-expanding metal stent that is produced by a plain weaving technique, as is described in the aforementioned DE 103 35 649.

The insertion system 10 also comprises a tube 14 which keeps the stent 12 radially compressed in the distal part of the tube 14. In this state, the device 10 is introduced into a vessel and placed at the desired position in order to support the vessel with the aid of the stent.

The insertion system in FIG. 1 also has a grip 22 on which a pulling grip 26 and a thumb hole are also provided. Ends of the flange 21 are also shown, which have a grooved surface 23. FIG. 1 also shows a guide wire 16. With this guide wire 16, the insertion system 10 is introduced into a patient's blood vessel by the known Seldinger technique in order to release the stent 12 therein.

Figure 2B:
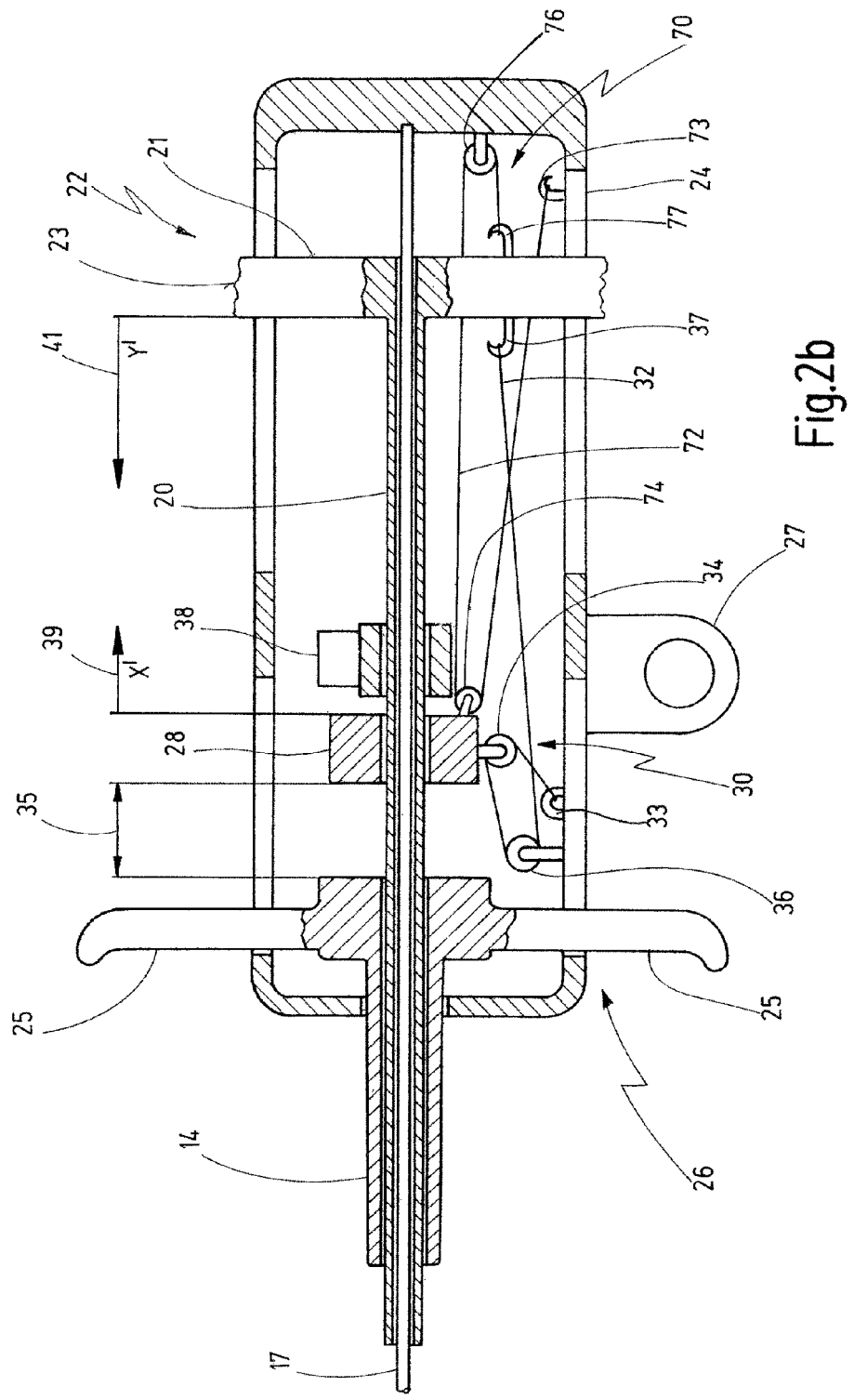
FIG. 2b shows the same longitudinal section as in FIG. 2a, with a further gear being provided in FIG. 2b.

In FIGS. 2a and 2b, the proximal end of the insertion system, in a first embodiment, is shown enlarged in a schematic longitudinal section.

The same elements as in FIG. 1 are identified by the same reference numbers.

In FIGS. 2a and 2b, the grip of the insertion system is designated overall by reference number 22 and comprises a housing 24. Moreover, reference number 26 designates a pulling grip which is arranged guidably in the housing 24 and which is coupled directly to the tube 14. The housing also accommodates a displaceable pushing element 20 which, in stent insertion systems, is also generally known as a pusher. Arranged in the pushing element 20 there is a stent carrier 17, which is anchored fixedly on the device 10 via the grip 22. The stent carrier 17 has an atraumatic tip 18 at its distal end. The guide wire 16 is guided in the stent carrier 17.

The housing 24 of the grip 22 also accommodates a movable element 28 which can be guided in the grip 22 and which is arranged to be displaceable along the pushing element 20 extending through the housing 24 of the grip 22.

The movable element 28 in FIG. 2a and FIG. 2b is coupled to the pushing element 20 via a cable pulley deflecting gear 30. The housing 24 of the grip 22 functions overall as a fixed bearing base for the deflection and retention functions of the cable pulley deflecting gear that are to be explained below. At its proximal end, the pushing element 20 has a flange 21, which in turn protrudes at least partially from the housing 24 of the grip 22. The ends of the flange 21 protruding from the housing 24 are designated by reference number 23.

As can be seen from FIG. 2a and FIG. 2b, the coupling between the movable element 28 and the pushing element 20 via the deflecting gear 30 has the effect of moving the pushing element 20 forward in the distal direction.

In FIG. 2 and FIG. 2b, the deflecting gear 30 has a tensioning thread 32 which is secured with one of its ends on the distal part of the housing 24 via an element in the form of an eyelet 33. The tensioning thread 32 is guided to the pushing element 20 via a first deflection element 34 provided on the movable element 28 and via a second deflection element 36 provided in the distal end of the housing 24. The deflection element 34 and the deflection element 36 are designed as pulleys, for example. The tensioning thread 32 is then secured with its second end on the pushing element 20 via a hook element 37. The hook element 37 is located on the flange 21 of the pushing element 20, specifically in a part of the flange 21 located inside the housing 24.

With the embodiment of the insertion system shown in part in FIG. 2a and FIG. 2b, and with the deflecting gear 30 of said system, a transmission ratio X'/Y' of 0.5 is achieved, where X' is the path of the movable element 28 relative to the path Y' of the proximal end of the pushing element 20, that is to say of the flange 21. This ratio is indicated by the arrows 39 and 41. The arrow 35 designates the path Z, which indicates the initial return path of the tube 14.

FIG. 2b also shows another gear 70, which works as an opposing gear of the cable pulley deflecting gear 30. This gear 70 can be provided such that the user also has the possibility of being able to reload the stent again by displacement of the movable element 28 distally. The further gear 70 also affords the user the possibility of releasing the stent by pushing together the movable element 28 and the flange 21.

The gear 70 also has a tensioning thread 72 which is secured with one of its ends on the proximal end of the housing 24 via an eyelet element 73. The tensioning thread 72 is guided to the pulling element 20 via a deflection element 74 provided on the movable element 28 and via another deflection element 76 provided on the proximal end of the housing 24. The deflection elements 74, 76 of the gear 70 are designed as pulleys, for example. The tensioning thread 72 is secured with its second end on the pushing element 20 via a hook element 77. The hook element is located on the flange 21 of the pushing element 20, specifically in the part of the flange 21 located inside the housing 24.

From the embodiment according to the invention shown in FIG. 2b, it will be seen that the opposing gear 70 is subjected to tension when the tensioning thread 32 of the cable pulley deflecting gear 30 is subjected to compression and comes loose. In this way, the gear transmission ratio between pulling grip 26 and movable element 28 remains constant, irrespective of which element or which combination of elements is actuated.

Figure 3A:
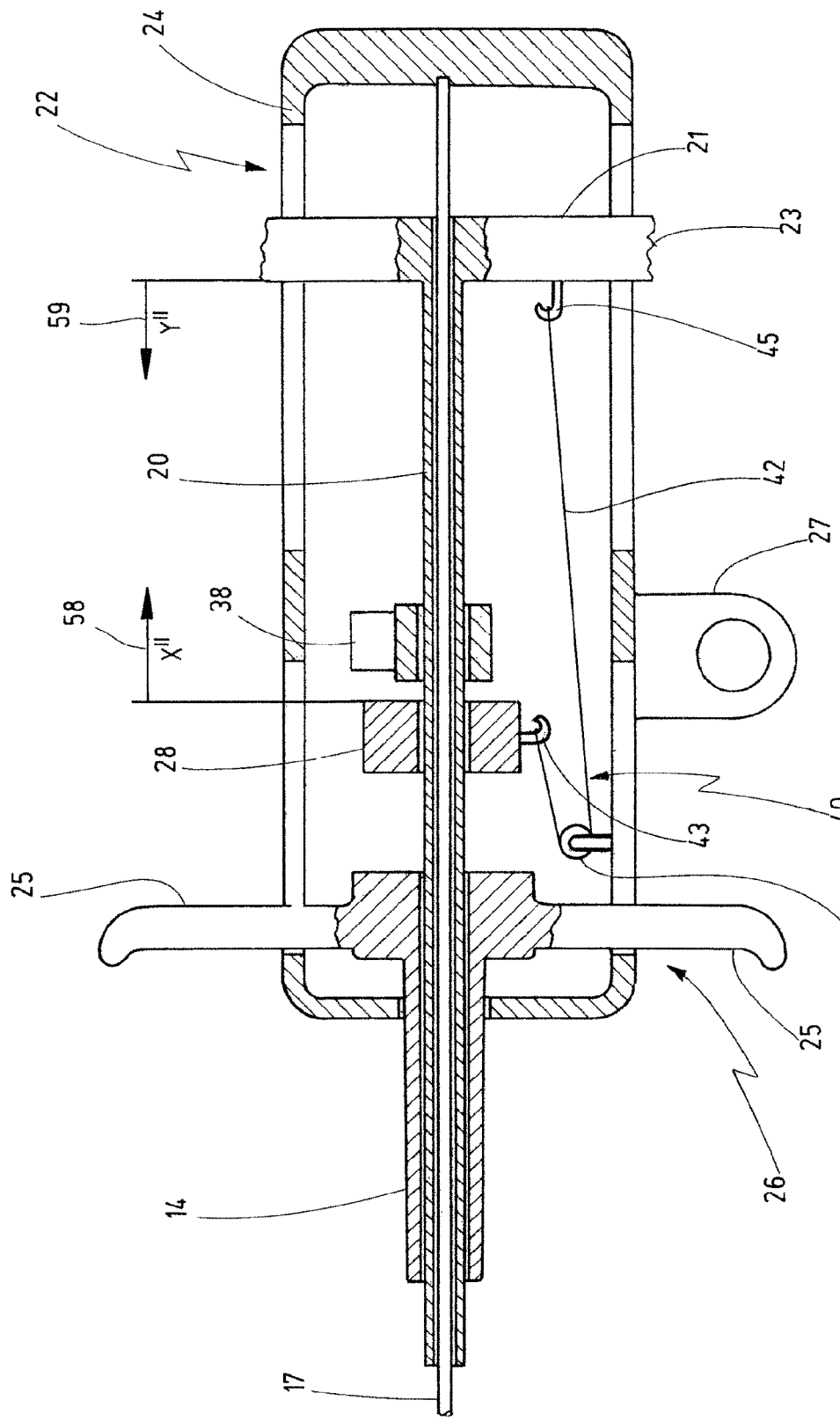
FIG. 3a shows, in a view similar to FIG. 2, a second illustrative embodiment of the novel insertion system.
Figure 3B:
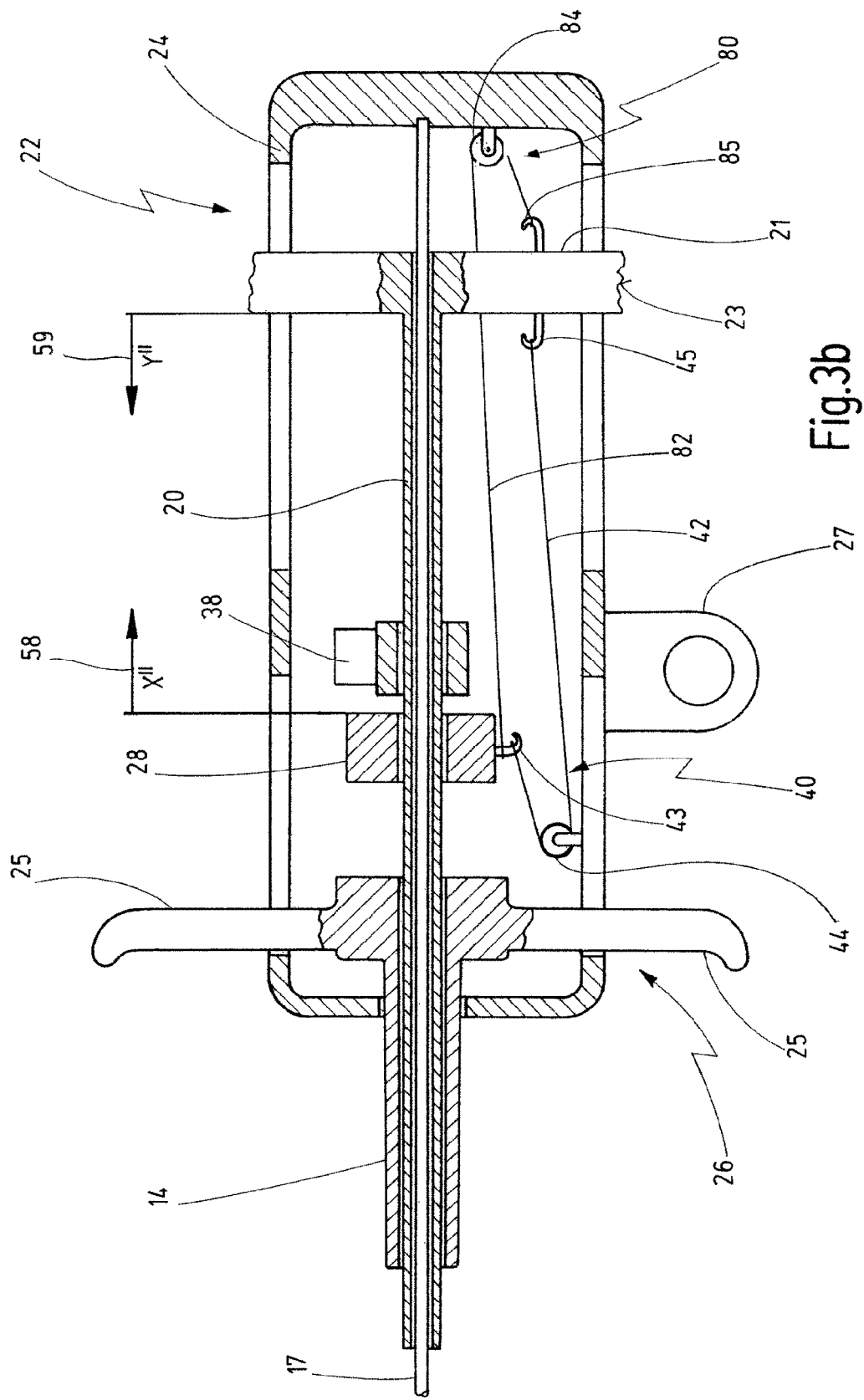
FIG. 3b shows the same longitudinal section as in FIG. 3a, with a further gear being provided in FIG. 3b.

FIGS. 3a and 3b another embodiment of the insertion system according to the invention in which, as in FIGS. 2a and 2b, only the grip 22 of the device is shown in longitudinal section. Here once again, the same elements are designated by the same reference numbers as in FIG. 1 and FIGS. 2a and 2b. Accordingly, the grip 22 in FIGS. 3a and 3b also has a pulling grip 26 which, in the position shown in FIGS. 3a and 3b, is mounted displaceably on the distal end of the housing 24 of the grip 22. The housing 24 also accommodates the pushing element 20 which, again as in FIGS. 2a and 2b, is arranged to be displaceable via the pulling grip. The pulling grip 26 is fixedly connected to the sleeve tube 14. The housing 24 further accommodates a movable element 28, which is mounted so as to be displaceable along the pushing element 20 or through which the pushing element 20 is designed to be displaceable. The device in FIGS. 3a and 3b also comprises, like the device in FIGS. 2a and 2b, a stop element 38, which is mounted in a removable manner in the housing 24.

The grip 22 also has, in its housing 24, a deflecting gear 40, which comprises a tensioning thread 42 secured with one of its ends on the movable element 28 via a hook element 43. Starting from the movable element 28, the tensioning thread 42 is then guided via a first deflection element 44, which is located in the distal area of the housing 24 of the grip 22. Via this first deflection element 44, the tensioning thread 42 is then guided to the pushing element 20, where it is secured with its other end via another hook element 45.

In this way, the movable element 28 is coupled to the pushing element 20. The arrows 58 and 59 indicate the direction of movement and length of travel of the movable element 28 (X) and of the pushing element 20 (Y). It will thus be seen that, in a movement of the movable element 28 in a proximal direction, as is indicated by the arrow 58, the pushing element 20, on account of the coupling to the movable element 28 via a deflecting gear 40, is displaced in the distal direction, as is indicated by the arrow 59.

With the deflecting gear shown in FIGS. 3a and 3b, and with the insertion system represented in FIGS. 3a and 3b, a transmission ratio of X'/Y'=1 can be achieved by virtue of the special arrangement of tensioning thread 42 and deflecting gear 44. The path of the movable element 28 is indicated by X', the path of the proximal end of the pushing element 20, thus of the flange 21, is indicated by Y'.

Like the embodiment in FIG. 2a, the embodiment shown in FIG. 3a can have a further gear 80, which has the same function as the gear 70 from FIG. 2b, namely that of providing the user with the possibility of releasing the stent by pushing together the movable element 28 and the flange 21. The embodiment with the second gear is shown in FIG. 3b.

FIG. 3b shows that the housing 24 has a gear 80 comprising a tensioning thread 82 which is secured with one of its ends on the movable element 28 via the hook element 43. Starting from the movable element 28, the tensioning thread 82 is then guided via a deflection element 84 which is located in the proximal area of the housing 24 of the grip 22. Via this deflection element 84, the tensioning thread 82 is then guided to the pushing element 20, where it is secured with its other end via a further hook element 85.

Figure 4A:
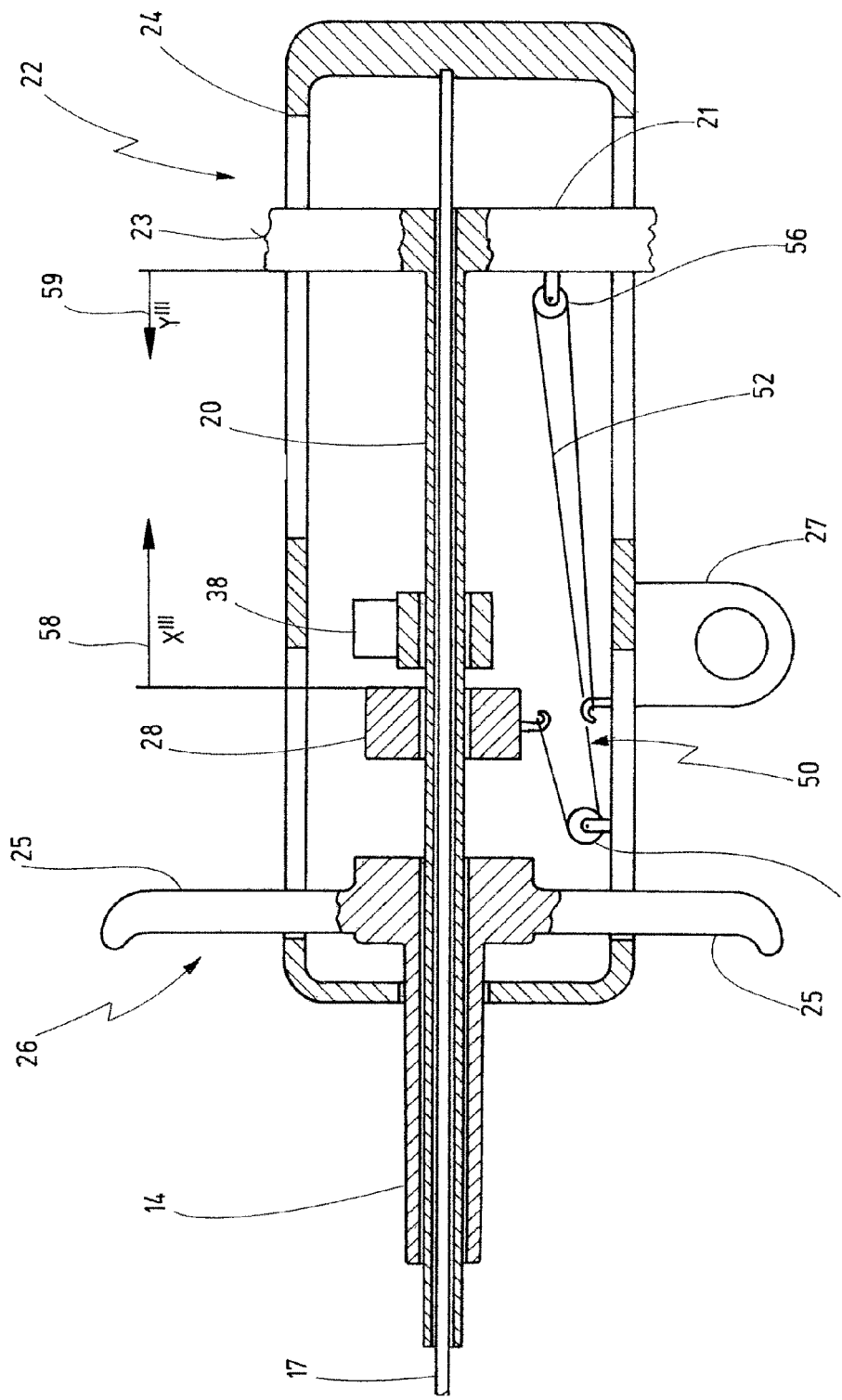
FIG. 4a shows, in a view similar to FIGS. 2 and 3, a third illustrative embodiment of the novel insertion system.
Figure 4B:
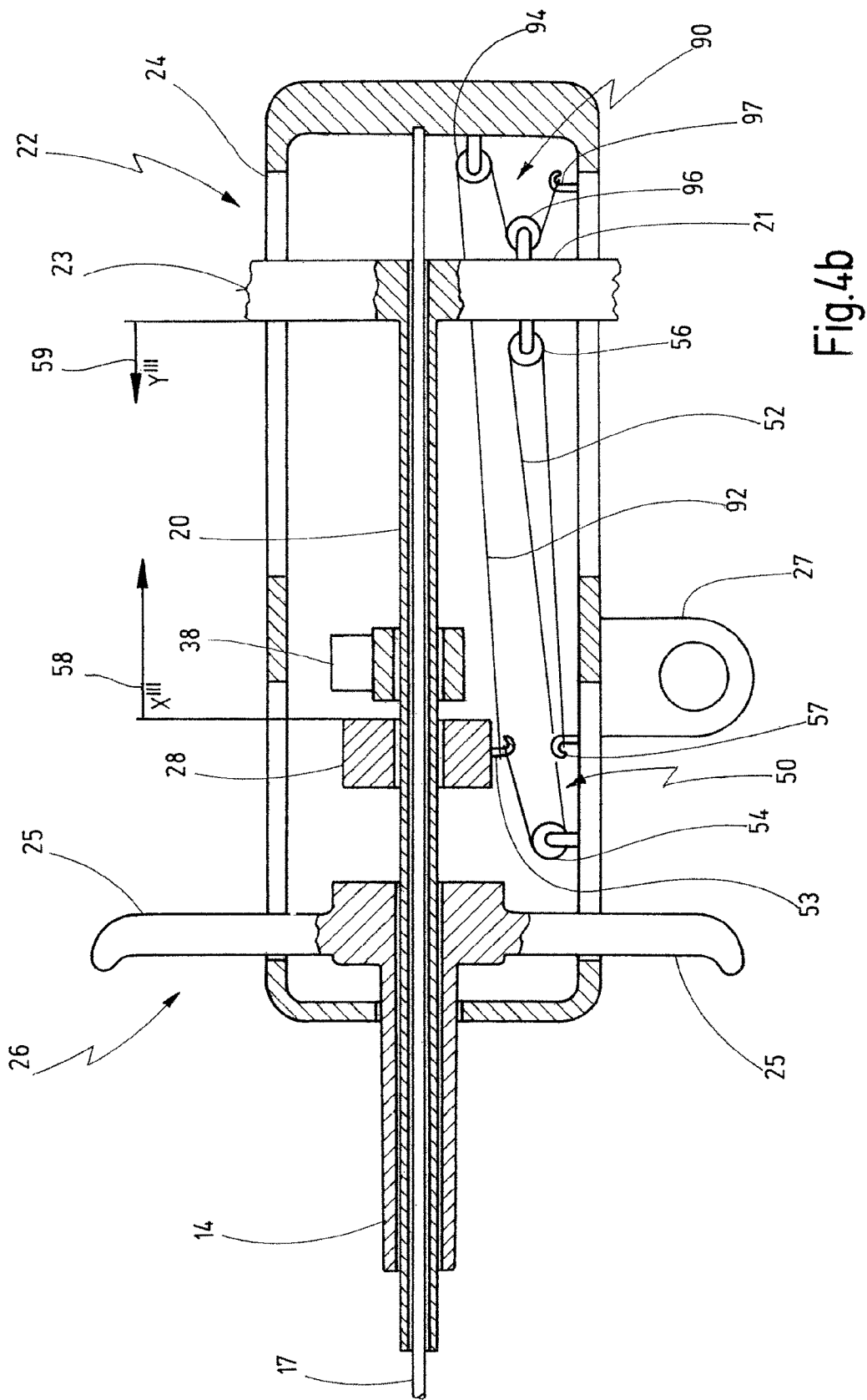
FIG. 4b shows the same longitudinal section of the illustrative embodiment as in FIG. 4a, with a further gear being provided in FIG. 4b.

FIGS. 4a and 4b show another embodiment of the insertion system according to the invention, and a particular design of the deflecting gear provided in the housing 24 of the device.

In FIGS. 4a and 4b, the same elements as in FIGS. 1 to 3 are provided with the same reference numbers. Thus, FIGS. 4a and 4b also show the longitudinal section through the housing 24 of the grip 22, said grip 22 having a pulling grip 26, which is displaceable in the housing 24 and which is fixedly connected or coupled to the tube 14. The housing 24 also accommodates a pushing element 20 which, at its proximal end, has a flange 21 whose ends protrude from the housing 24 of the grip 22 and have a grooved surface 23. With this grooved surface 23, it is possible, as in FIGS. 1 to 3 also, to grip the pushing element 20 by hand and move it both in the proximal direction and also in the distal direction. A movable element 28 is mounted displaceably along the pushing element 20, or is guided through the movable element 28 and the tensioning grip 26. The movable element 28 is coupled with the pushing element 20 via a deflecting gear 50.

The deflecting gear 50 has a tensioning thread 52 which is secured with one of its ends on the movable element 28 via a hook element 53. The tensioning thread 52 is guided via a first deflection element 54 provided in the distal area of the housing 24 of the grip 22. From this first deflection element 54, the tensioning thread 52 is guided to a second deflection element 56 provided on the proximal end of the pushing element 20. FIGS. 4a and 4b show that the second deflection element 56 is located on the flange 21 of the pushing element 20. From this second deflection element 56, the tensioning thread 52 is guided back into the distal area of the housing 24, where it is secured with its second end on another hook element 57.

FIGS. 4a and 4b also show that a displacement of the movable element 28 in the proximal direction, as is indicated by the arrow 58, causes a displacement of the pushing element 20 in the distal direction, which is shown by the arrow 59. In the device in FIG. 4, the path X' traveled by the movable element 28 and the path Y' traveled by the proximal end of the pushing element 20 have a transmission ratio of X'/Y'=2. This means that the movable element 28 has traveled twice as far as the pushing element 20.

FIG. 4b shows, as in FIGS. 2b and 3b, the embodiment with a further gear. The further gear 90 has a tensioning thread 92 which is secured with one of its ends via the hook element 53 on the movable element 28. The tensioning thread 92 is guided via a deflection element 94 located in the proximal area of the housing 24 of the grip 22. From this deflection element 94, the tensioning thread 92 is guided to a deflection element 96, which is located on the proximal end of the pushing element 20. The deflection element 96 is mounted on the flange 21 of the pushing element 21. From this deflection element 96, the tensioning thread 92 is guided back into the proximal area of the housing 24, where it is secured with its second end on another hook element 97. The deflection elements 94 and 96 are also designed as pulleys in FIG. 4b.

All of the embodiments of the device according to the invention shown in FIGS. 1 to 4 have a gripping element 27, which is mounted on the outside of the housing 24 of the grip 22 and which is designed as a thumb hole in FIGS. 1 to 4. With the aid of the gripping element 27, the grip 22 and with it the entire insertion system can be securely fixed in the user's hand.

Moreover, in all of the embodiments shown in FIGS. 1 to 4, the housing 24 accommodates a stop element 38, which can prevent direct abutment of the movable element 28 with the proximal end of the pushing element 20, in other words with the flange 21 in the present case. In all of the embodiments, the pushing element 20 is guided through the stop element 38, the movable element 28 and the tensioning grip 26. All the elements, that is to say the pushing element 20, the movable element 28, the stop element 38 and the tensioning grip 26, can be displaced relative to one another, with, as has been described, the pushing element 20 being guided displaceably through the other elements.

The stop element 38 is mounted releasably in the housing 24 and can be withdrawn for final release of the stent 12 and for causing direct contact between the movable element 28 and the proximal end of the pushing element 20, that is to say the flange 21.

Figure 6A:
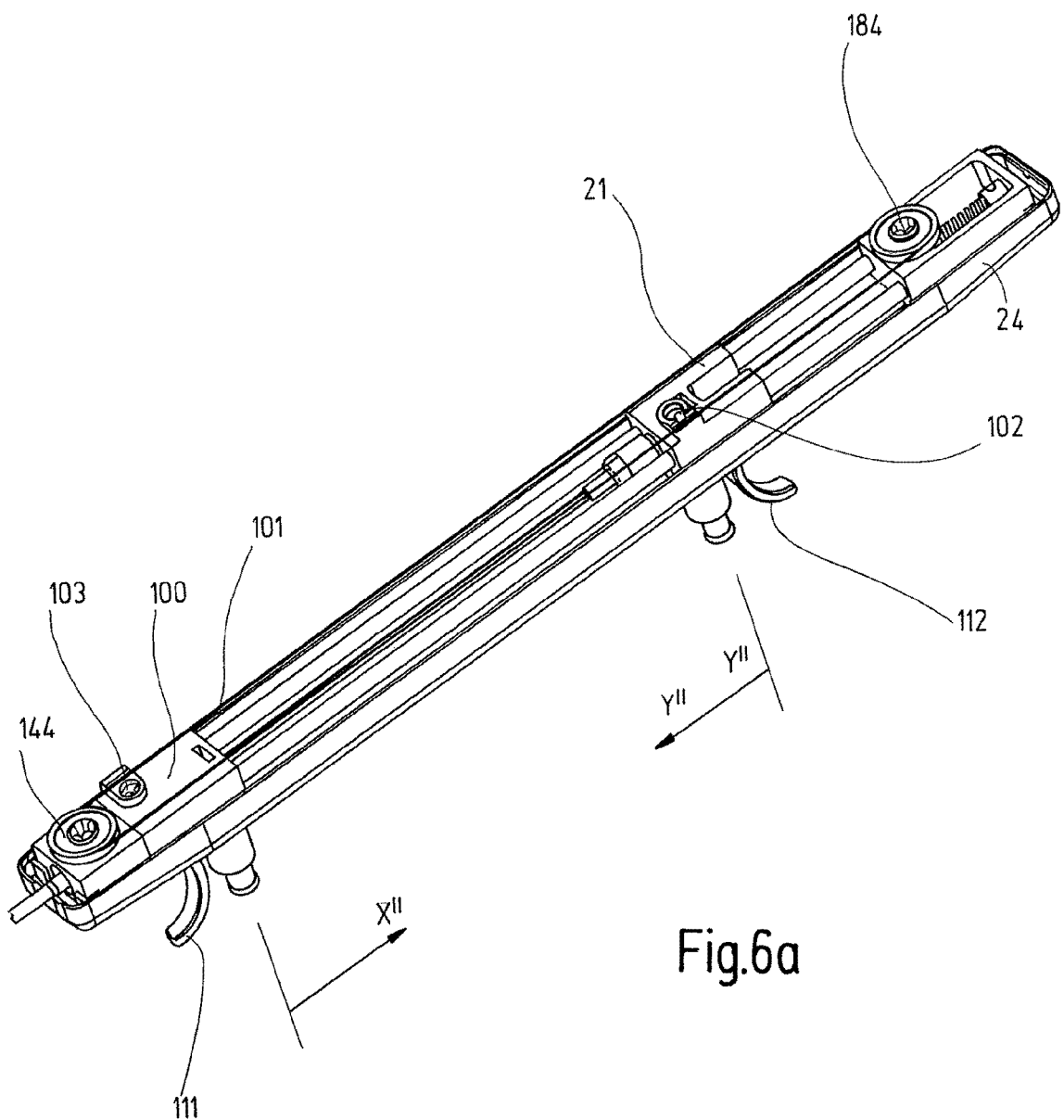
FIG. 6a shows a schematic, perspective view (not true to scale) of yet another embodiment of the proximal (grip) portion of the insertion system according to the invention, in the unactuated state and therefore before release of the stent (not shown), the housing being shown here only in part so as to better illustrate the interior of the housing.
Figure 6B:
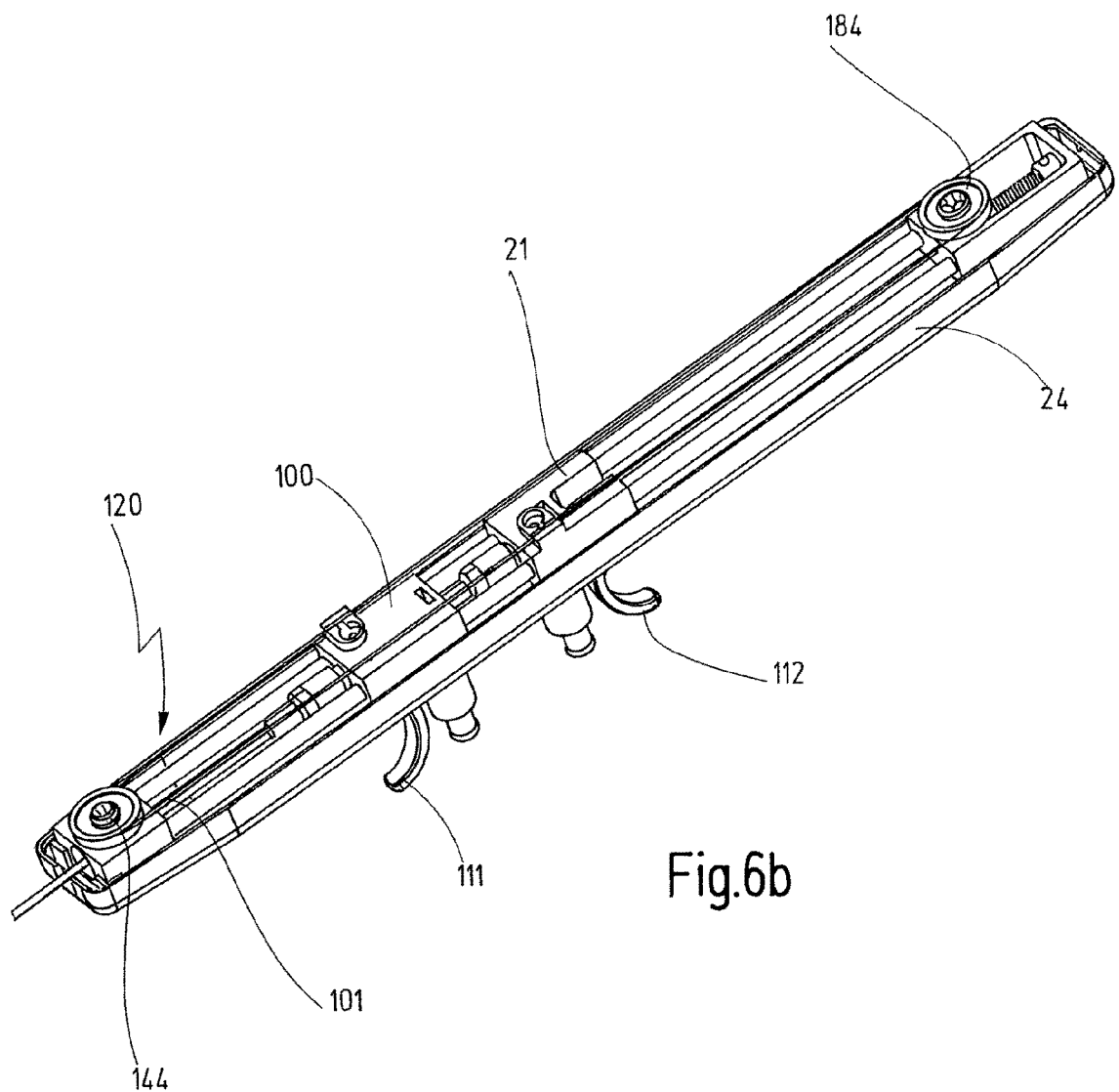
FIG. 6b shows the embodiment from FIG. 6a, but here the movable element and the pushing element are brought together by actuation of the device, as a result of which the stent (not shown) is released.
Figure 7A:
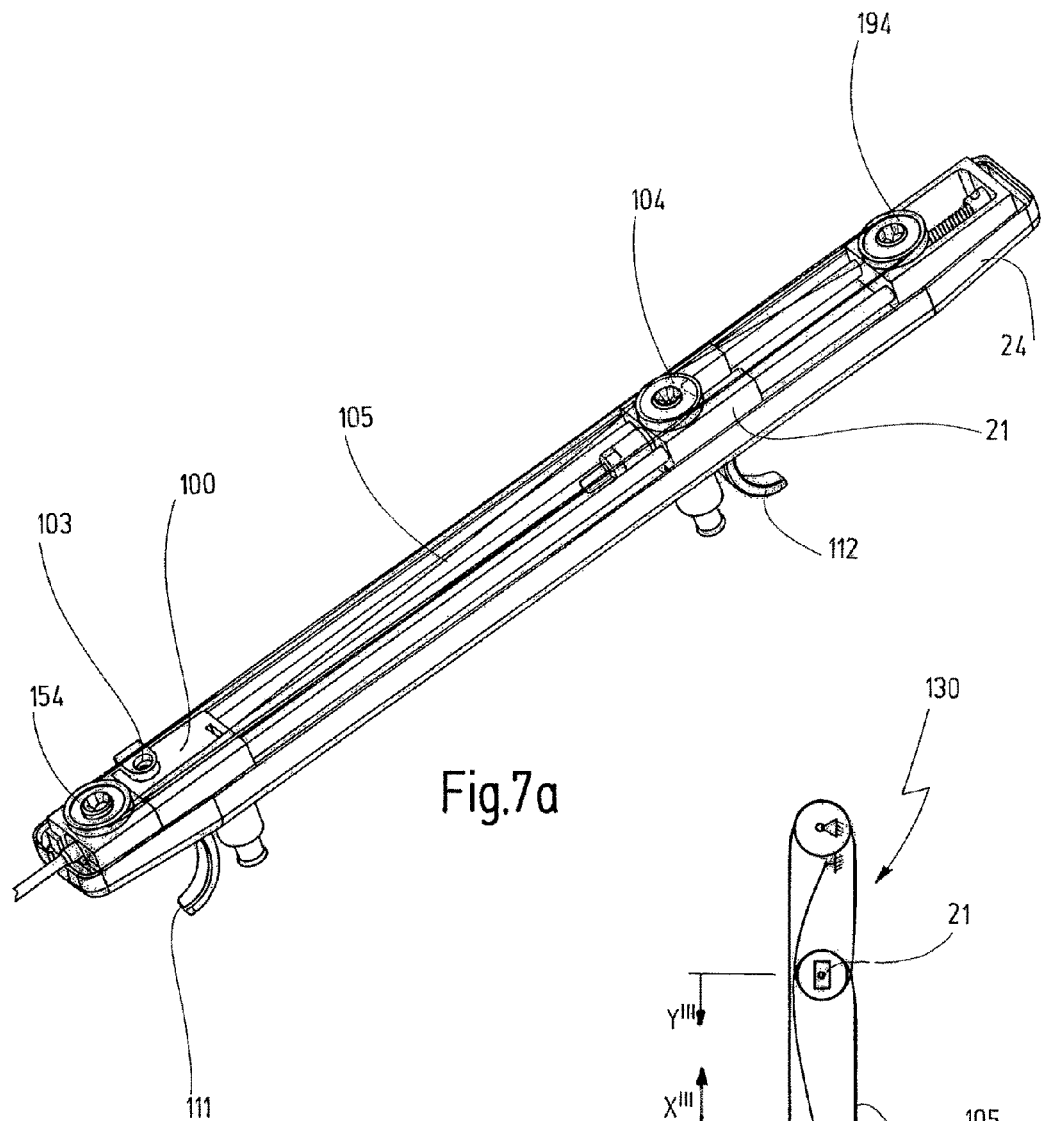
FIG. 7a shows a schematic, perspective view (not true to scale) of yet another embodiment of the proximal (grip) portion of the insertion system according to the invention, in the unactuated state and therefore before release of the stent (not shown), the housing being shown here only in part so as to better illustrate the interior of the housing.
Figure 7B:
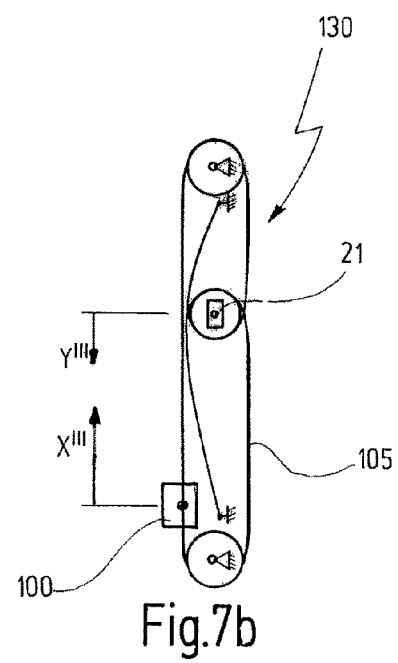
FIG. 7b shows a schematic view of the course of the tensioning thread.
Figure 7C:
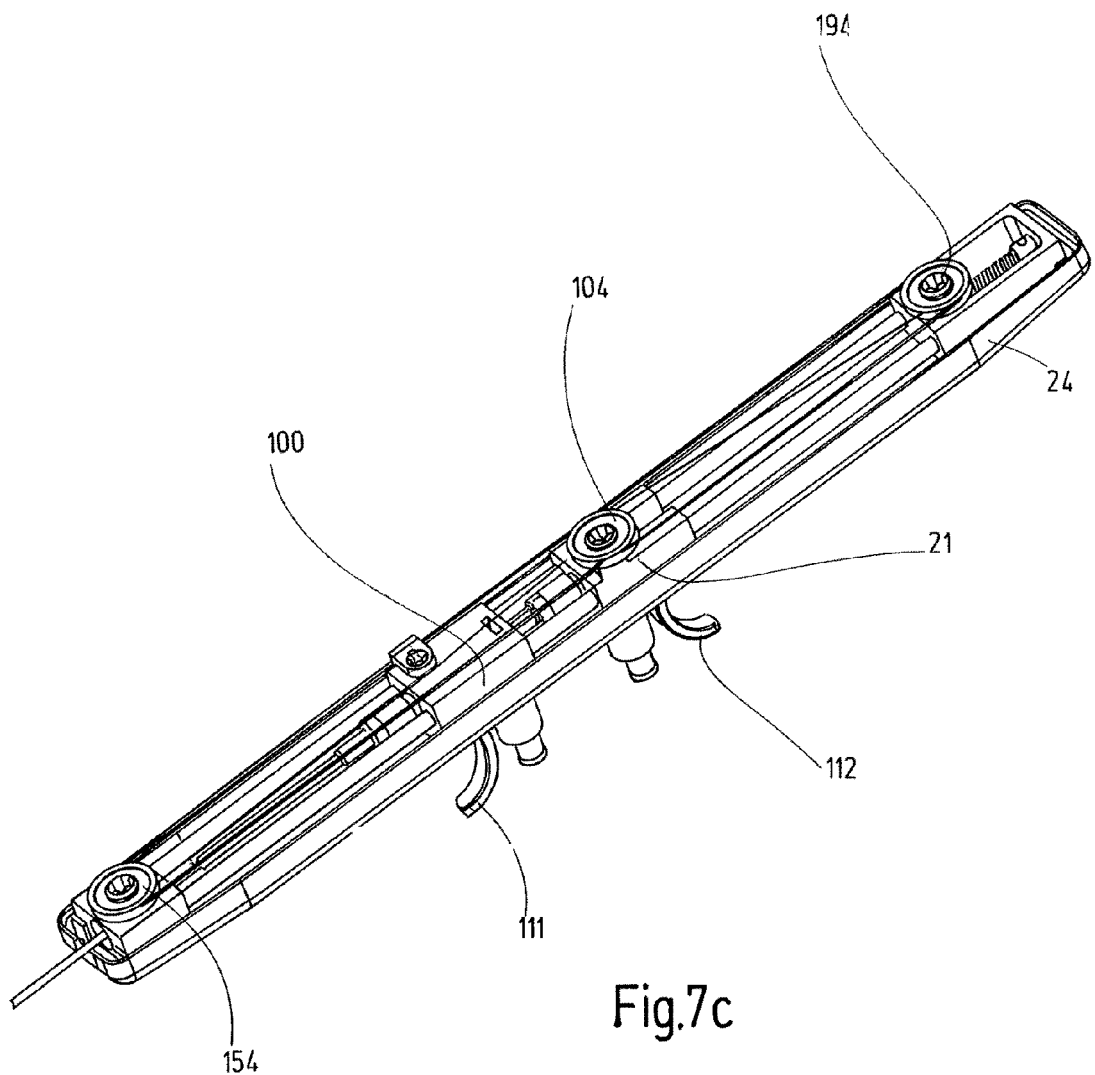
FIG. 7c shows the embodiment from FIG. 7a, but here the movable element and the pushing element are brought together by actuation of the device, as a result of which the stent (not shown) is released.

FIGS. 5 to 7 show developments of another embodiment of the device according to the invention. In these developments, the deflection elements/pulleys and hook elements and tensioning threads provided in the previously described embodiments have been combined. Moreover, the pulling grip described in FIGS. 2 to 4 has been combined with the movable element as one structural part, both elements in FIGS. 5 to 7 now forming a tensioning element or tensioning flange.

In FIGS. 5 to 7, elements identical to those shown in FIGS. 2 to 4 have been designated by the same reference numbers. Moreover, the same reference numbers are used for elements that are equivalent in FIGS. 5 to 7.

In FIG. 5a, reference number 22 designates the overall grip in the development of the device according to the invention, with a housing 24. To illustrate the elements provided in the housing 24, part, in this case half, of the housing 24 in FIG. 5 has been removed. Reference number 100 designates the tensioning element, which is here designed in the form of a flange. The deflecting gear in this embodiment is designated overall by reference number 110. The tensioning element 100 is connected directly to the sleeve tube for the stent that is to be released (the latter elements are not shown). The tensioning element 100 has elements protruding from the housing 24, with reference number 111 designating an element in the form of a trigger. In the embodiment shown, the tensioning element 100 is designed as a flange and has a rotatable pulley 106 that is mounted flat on the tensioning element 100 and serves as deflection element.

As in FIGS. 2 to 4, reference number 21 in FIG. 5a designates the proximal end of the pushing element 20 designed as a flange. The flange 21 here has a clamp element 102, which fixes a tensioning thread 107 on the flange 21. Like the tensioning element 100, the flange has elements that protrude from the housing 24, with an element 112 designed here too as a trigger. At the proximal and distal ends of the housing 24 there are further deflection elements 136, 176, which are designed in the manner of a fixed pulley and lie flat. The deflection elements 136 and 176 also serve to secure the ends of the tensioning thread 107. Starting from the distal end of the housing 24, on which one of its ends is secured, the tensioning thread 107 is guided via the pulley 106 provided on the tensioning element 100. The tensioning thread 107 is then placed round the deflection element 136 located at the distal end of the housing 24. The tensioning thread 107 extends onward to the flange 21, or through the clamp element 102 provided on the flange 21, and back to the distal end of the housing 24, where it is secured with its second end. The tensioning thread 107 is fixed on the flange 21 via the clamp element 102. The course of the tensioning thread 107 is shown schematically in FIG. 5b.

The ends of the tensioning thread 107 can be secured, for example, by means provided on the deflection element.

Figure 5C:
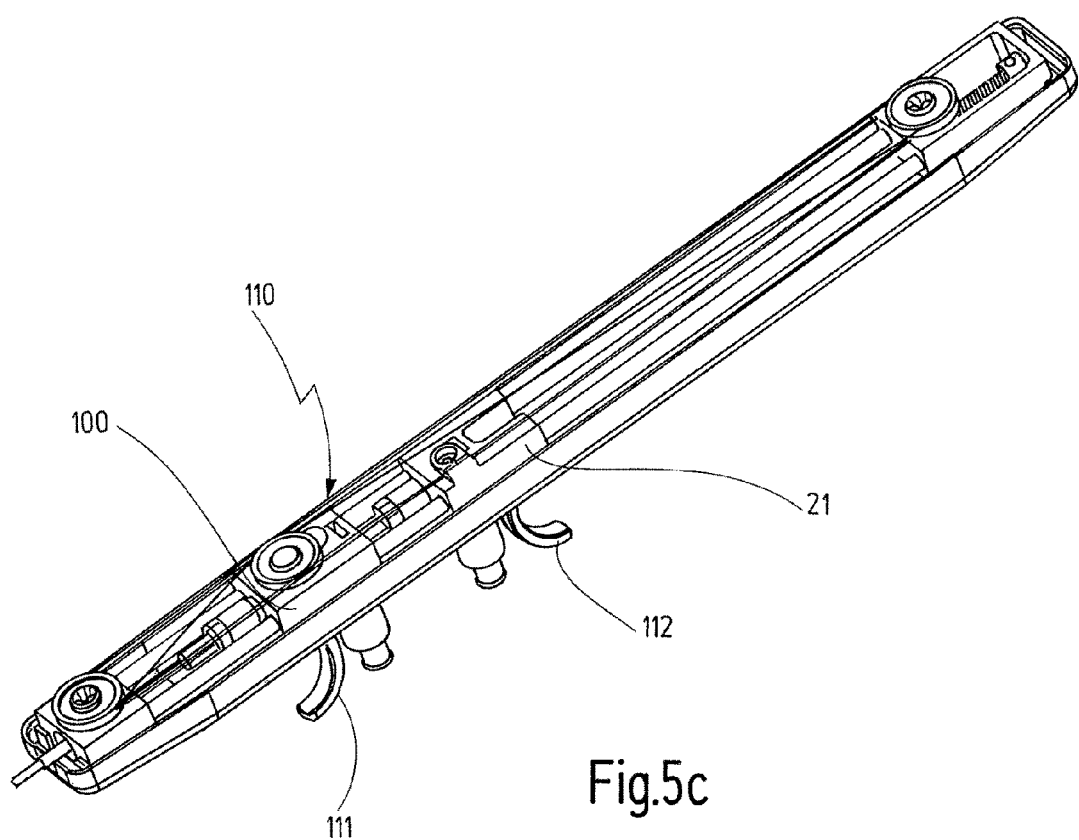
FIG. 5c shows the embodiment from FIG. 5a, but here the movable element and the pushing element are brought together by actuation of the device, as a result of which the stent (not shown) is released.

In the start position, that is to say before release of the stent, the tensioning element 100 is located in the area of the distal end of the housing 24, at a certain distance away from the proximal end of the pushing element 21. Upon actuation of the trigger 111 or 112, or, for simpler handling, of both triggers 111, 112, the tensioning element 100 is guided in the proximal direction, i.e. toward the user. This is shown in FIG. 5c, from which it will be seen that, upon actuation of the trigger 111, the tensioning element 100 and the proximal end of the pushing element 20, that is to say the flange 21, move toward each other. On account of the coupling of the tensioning element 100 to the pushing element 20 via the elements of the deflecting gear.

It will be seen from FIGS. 5b and 5c that a transmission ratio X'/Y' of 0.5 is achieved with the embodiment shown here, where X' is the path of the movable element 28 or tensioning element 100 relative to the path Y' of the flange 21 of the pushing element 20.

FIG. 6 shows another development of an embodiment of the device according to the invention similar to the embodiment shown in FIG. 5, the deflecting gear here being designated overall by reference number 120. In FIG. 6 too, in order to illustrate the elements provided in the housing 24, part, in this case half, of the housing 24 has been removed. In this embodiment, the flange-shaped tensioning element 100, which is likewise coupled to the (sleeve) tube, has no deflection element, but instead a clamp element 103 into which a tensioning thread 101 is clamped and thereby fixed on the tensioning element 100. The tensioning thread 101 is in a loop shape in FIG. 6 and extends around a deflection element 144 at the distal end of the housing 24 and around a deflection element 184 at the proximal end of the housing 24. The tensioning thread 101 is further fixed on the flange 21 of the pushing element 20 via a clamp element 102. Tensioning element 100 and flange 21 each have a trigger element 111, 112, via which the elements can be actuated. The flange 21 can lie more to the right or more to the left with respect to FIG. 6a, depending on the loaded stent length.

FIG. 6a shows the starting state, that is to say the state of the insertion system in which the stent is not yet released. The release is effected by actuation of the trigger 111 or 112 or of both triggers 111, 112, as a result of which the tensioning element 100 and the flange 21, that is to say the proximal end of the pushing element 20, are moved toward each other. The stent is released in this way. This state is shown in FIG. 6b. With the embodiment shown in FIG. 6, a transmission ratio X"/Y" of 1 can be achieved, where X" is the travel of the movable element 28 or tensioning element 100 relative to the travel Y" of the flange 21 of the pushing element 20.

In FIG. 7, half of the housing 24 has again been removed for better illustration. The deflecting gear is designated overall by reference number 130 in FIG. 7. Here, the tensioning element 100 has a clamp element 103 via which a tensioning thread 105 can be fixed with the tensioning element 100. The flange 21 of the pushing element 20 has a rotatable pulley 104, which is secured flat on the flange 21. The proximal end and the distal end of the housing 24 each have a deflection element in the form of fixed pulleys/disks 154, 194. The tensioning thread 105 is secured with one of its ends on the distal end of the housing 24 and from there is guided around the rotatable pulley 104 provided on the flange 21. From there, the tensioning thread 105 is again guided round the deflection element 154 provided at the distal end of the housing 24, onward to the deflection element 194 provided on the proximal end of the housing 24, then once again round the pulley 104 of the flange 21 and, finally, is secured with its other end on the distal end of the housing 24.

The ends of the tensioning thread 105 can be secured, for example, by means provided on the deflection element.

FIG. 7b is a schematic view of the course of the tensioning thread. FIG. 7b, like FIGS. 5c and 6b, shows the state of the system after release of the stent, according to which, by actuation of the triggers 111, 112, or of one of the triggers 111, 112, the two elements, namely tensioning element 100 and flange 21, are moved toward each other. In the embodiment shown in FIG. 7, a transmission ratio X'''/Y''' of 2 can be achieved, where X''' is the travel of the movable element 28 or tensioning element 100 relative to the travel Y''' of the flange 21 of the pushing element 20.

It will be seen from FIGS. 5 to 7 that the pushing element (pusher) moved in the distal direction pushes the stent out of the sleeve, while at the same time the sleeve is also actively removed from the stent by virtue of the coupling to the tensioning element 100, as a result of the movement of the latter in the proximal direction.

FIGS. 8A to 8E are schematic views showing the sequence of the release of a stent 12 by means of an insertion system shown in FIGS. 1 to 7. This release mechanism will be explained in detail below with reference to FIGS. 8A to 8E, said release mechanism of the stent 12 being identical in all of the embodiments shown in FIGS. 1 to 7. In FIGS. 8A to 8E, the upper half of the figure, indicated by a), shows the release status of the stent, and the lower half of the figure in FIGS. 8A to 8E, indicated by b), shows the corresponding status at the grip 22 of the insertion system.

FIGS. 8A to 8E show an illustrative embodiment of the housing 24 of the grip 22 of all the embodiments of the device shown in FIGS. 1 to 7. The housing 24 has a channel-shaped, rail-type recess 62 via which the elements of the pulling grip 26, movable element 28 and pushing element 20 lying outside the housing 24 are guided displaceably in the housing 24. Such elements are, for example, screws and nuts that are needed for mounting the pulling grip 26, the movable element 28 and the pushing element 20 in or on the housing. The stop element 38, which partially protrudes from the housing, as is shown in FIGS. 5 to 8, is also guided in this recess.

Moreover, an elongate recess 64 is located along the side of the housing 24 of the grip 22, and the ends of the flange 21 of the pushing element 20 and the gripping tab 25 of the pulling grip 26 are guided displaceably in said recess 64.

As has already been described above, for the purpose of inserting a stent 12 into a body vessel, the stent is radially compressed in a sleeve or a tube 14 in order to achieve the smallest possible diameter. This state of the stent is shown in the upper half of each of FIGS. 8A to 8E. Because of its design as a metal stent, the stent 12 presses against the tube 14 with a certain force. The tube 14 is coupled fixedly to the pulling grip 26, which is mounted displaceably in the housing 24 of the grip 22 of the insertion system. The pulling grip 26 has two gripping flanges 25 protruding from the housing 24. The pulling grip 26 can be easily taken hold of via the gripping flanges 25.

The user, for example the operating surgeon, now holds the grip 22 in one hand and, for example, places his thumb in the gripping element 27. It will be understood that the gripping element 27 can have any configuration that permits a secure hold of one or more fingers on the grip 22. In a next step, the middle finger and index finger of the user can be placed on the pulling grip 26 or the gripping flanges 25 thereof which protrude from the housing 24. It will be understood that it is not necessary for the middle finger and index finger always to hold the pulling grip; for example, the other hand can be used for this.

In order to release the stent 12, the middle finger and index finger are pulled toward the thumb, that is to say in the proximal direction. The pulling grip 26 is initially pulled back by an initial return path Z of the sleeve tube 14. This is shown in FIG. 6. FIG. 6a shows that, as a result of this movement, the distal end of the stent 12 comes free and, on account of its spring action, places itself against the vessel wall distally of the stenosis or of the vascular lesion.

When the pulling grip 26 is pulled back further, the movable element 28, in addition to the tube 14, is then also entrained in the proximal direction in the housing 24 of the grip 22. The stop element 38, which is mounted movably along the pushing element 20 in the housing 24, can also be entrained in this movement.

The movable element 28 is coupled via a deflecting gear 30, 40 or 50 to the proximal end of the pushing element 20 or to the flange 21 of the latter. The housing 24 of the grip 22 functions as a firm bearing base for the deflecting gears in the various embodiments described herein. The coupling between the movable element 28 and the pushing element 20/flange 21 via the deflecting gears 30, 40 or 50 thus results in a forward movement of the pushing element 20 in the distal direction. This is shown in FIG. 8C.

Figure 8A:
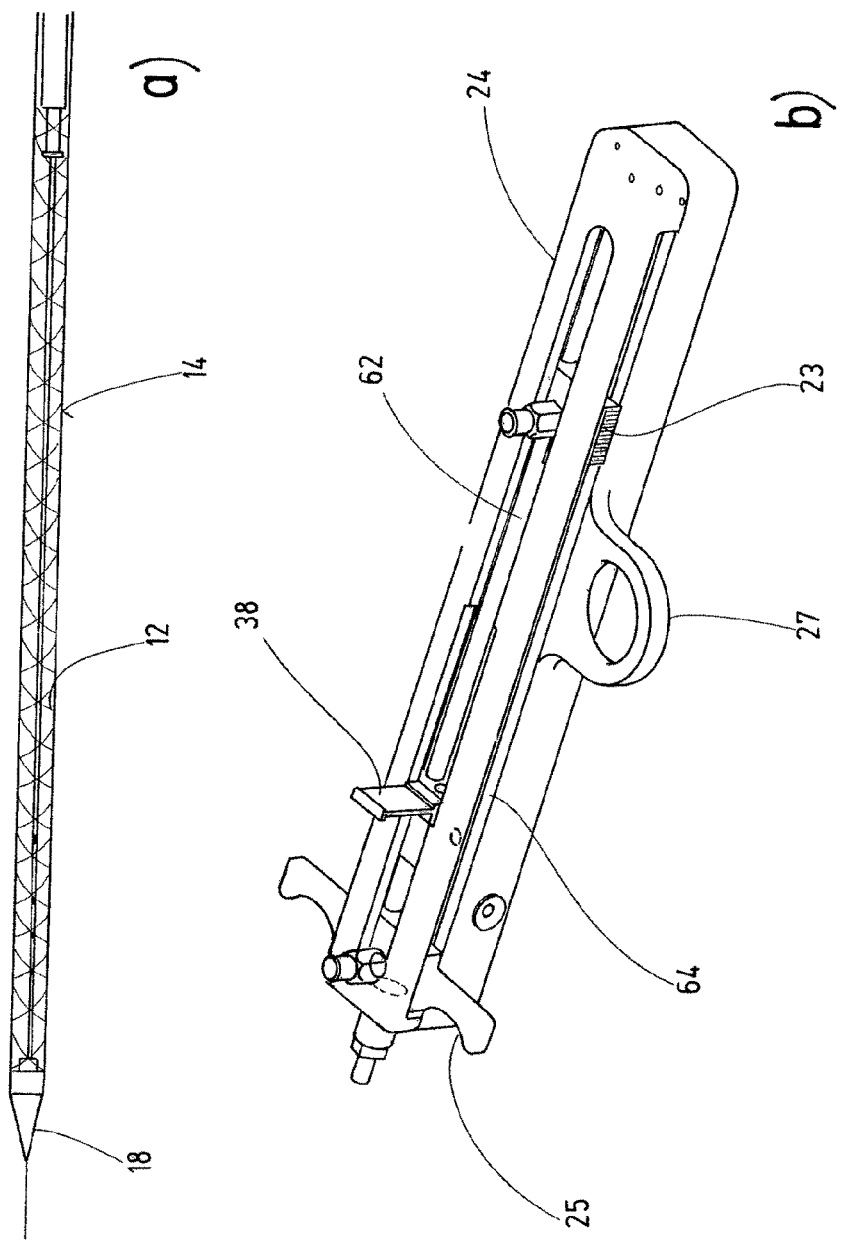
FIG. 8A shows a perspective plan view (a) of the grip of the insertion system, and the side view (b) of the distal portion of the insertion system, in a position in which the stent is in a form compressed by the tube.
Figure 8B:
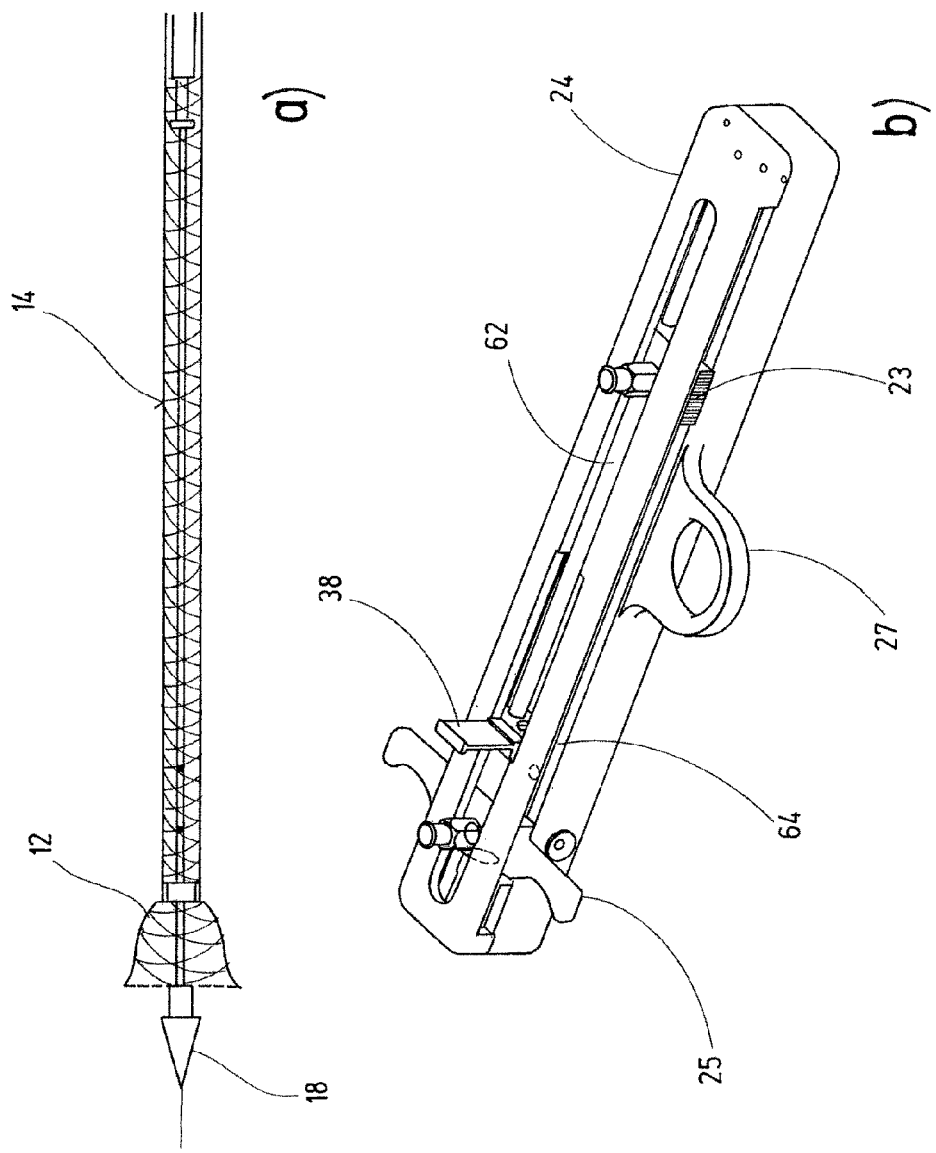
FIG. 8B shows a view similar to FIG. 8A, with the stent being released by a short distance at the distal end.
Figure 8C:
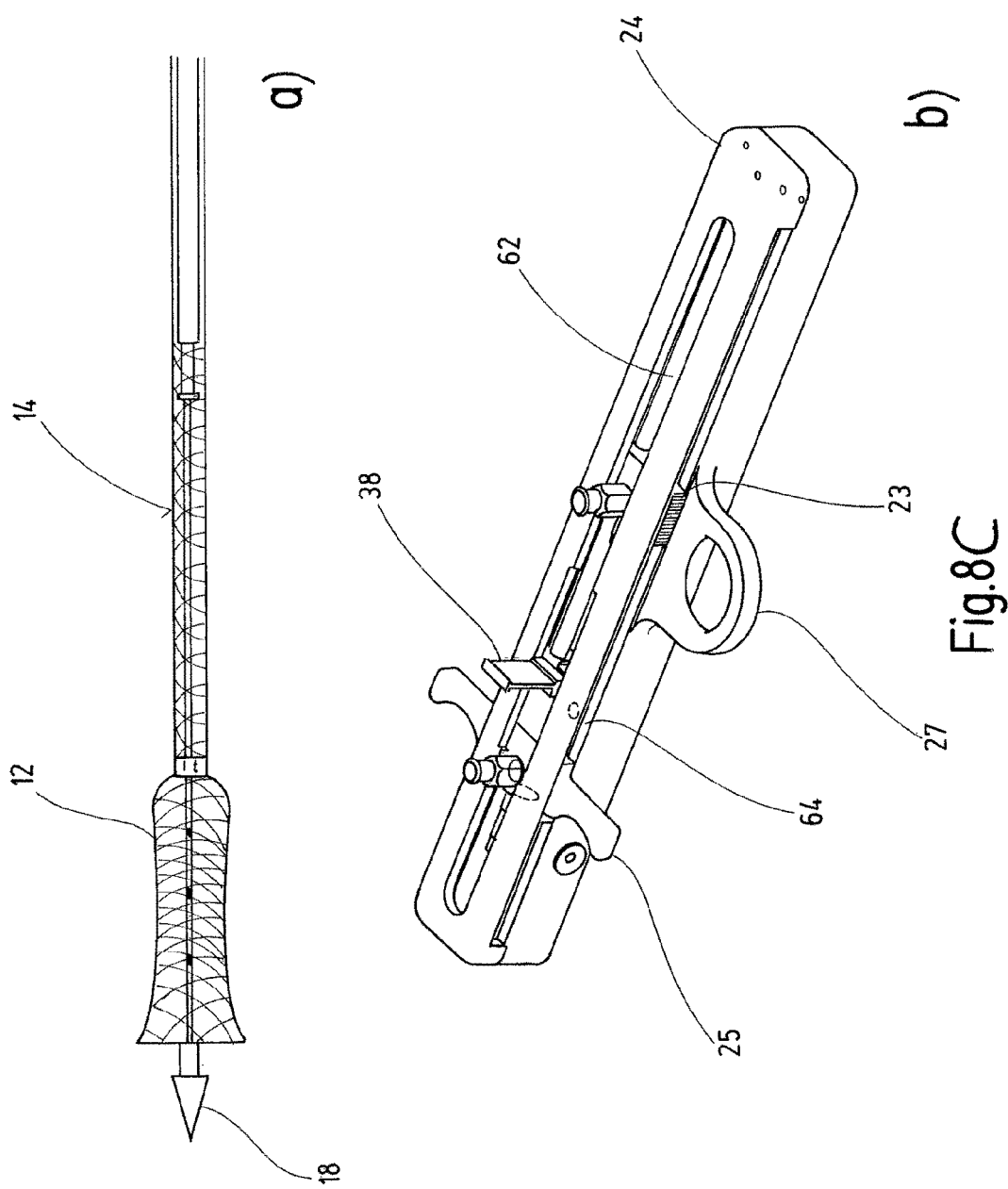
FIG. 8C shows a view similar to FIG. 8A, depicting the next step in the release of the stent.

In FIG. 8C, in the upper half indicated by a), the return movement of the tube 14 and the opposite action of the pushing element 20 mean that the stent 12 has now already been released to a greater extent.

Figure 8D:
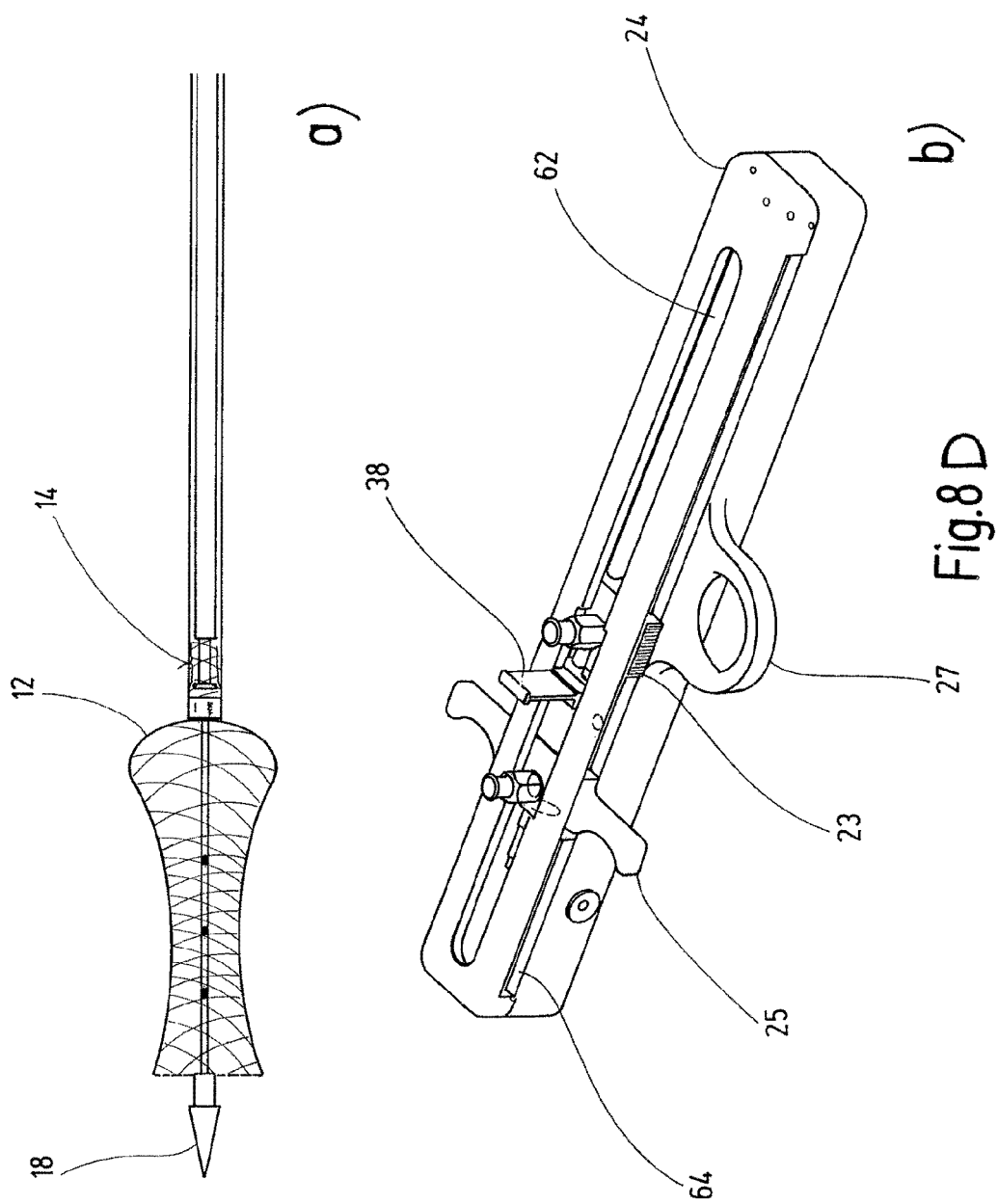
FIG. 8D shows a view similar to FIG. 8A, depicting the stop element that prevents direct abutment of the movable element with the pushing element stop.

FIGS. 8A to 8E show that, in subsequent steps, the pulling grip 26 and the entrained movable element 28, when pulled back further in a proximal direction, meet the flange 21 of the pushing element 20 or are prevented from direct contact by a stop element 38. This has the effect that the movable element 28 and the proximal end of the pushing element 20, that is to say the flange 21 of the pushing element 20, do not directly abut. This state is shown in FIG. 8D.

This configuration ensures that a sufficient part of the proximal end of the stent 12 remains lying in the tube 14 and fixed on the pushing element 20. This is shown in FIG. 8A, where the stent is not yet fully released at its proximal end. The lower half of FIG. 8D shows the parallel "state" of the grip 22. Here, the pulling grip 26, the movable element 28, the stop element 38 and the flange 21 of the pushing element 20 are in contact in this sequence. In this phase, the stent 12 can, if necessary, be pulled back completely into the insertion system. For this purpose, the flange 21 of the pushing element 20 simply has to be taken hold of via its ends protruding from the housing 24 and pulled in the distal direction. The deflecting gear 30, 40 or 50 is now reversed and presses the movable element 28 and pulling grip 26 with the sleeve tube 14 in the distal direction. The stent 12 is in this way gently detached from the vessel wall and at the same time pulled back into the insertion system and into the tube 14.

Figure 8E:
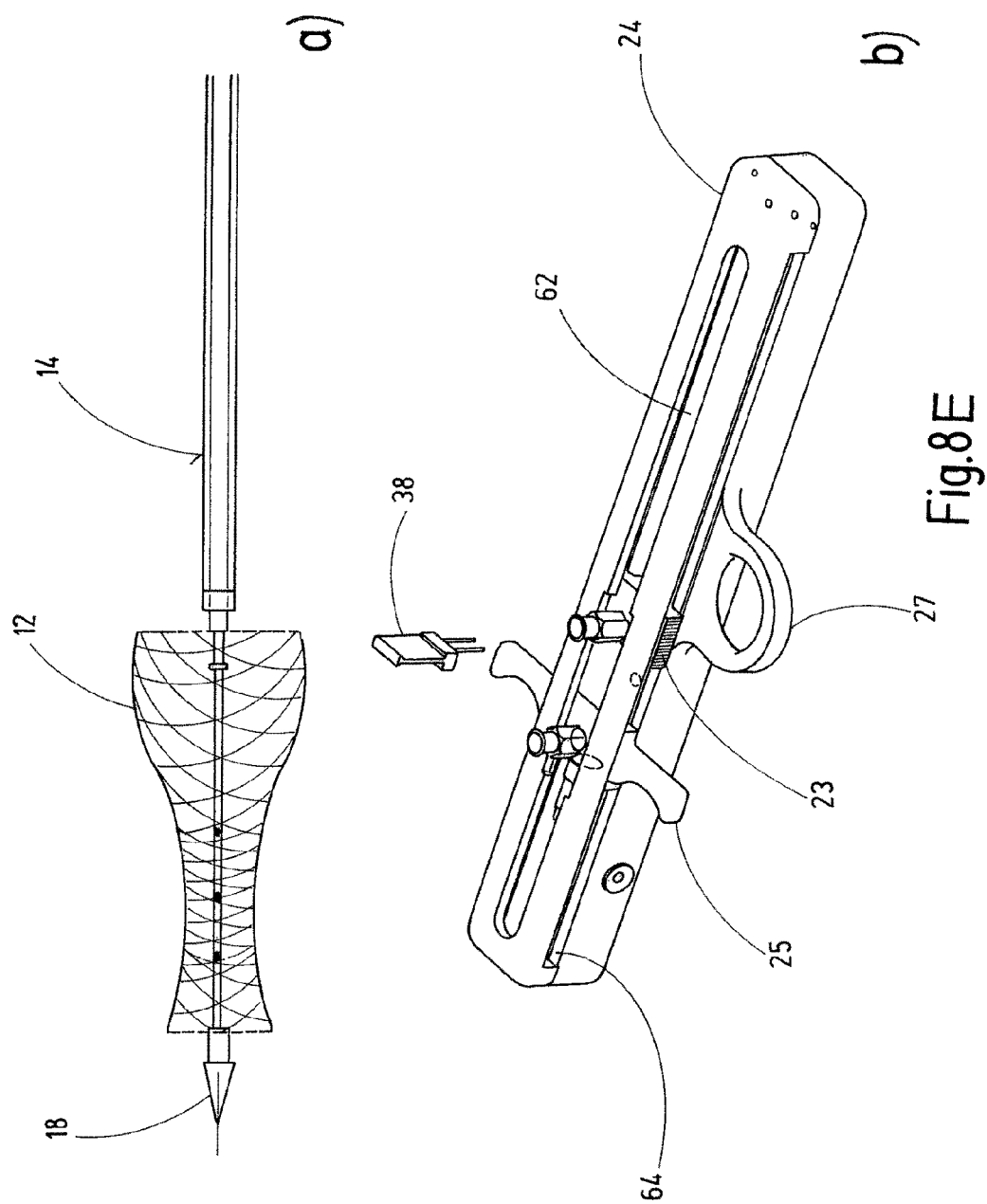
FIG. 8E shows a view similar to FIG. 8A, but the stop element has been removed here, as a result of which the movable element can be pulled back completely in the proximal direction to abut against the pushing element, and the stent can in this way be released.

If the stent 12 is to be released fully, the stop element 38 between the movable element 28 and the flange 21 of the pushing element 20 is withdrawn. The movable element 28 can then be moved fully in the proximal direction via the pulling grip 26. This step is shown in FIG. 8E. It will be seen from the upper half of FIG. 8E that the stent 12 is now fully released, and FIG. 8E, lower part, shows the parallel state of the grip 22, from which the stop element 38 has been removed.

Upon removal of the insertion system from the vessel, the guide wire 16 can now be pulled out carefully in the proximal direction through the expanded stent.

In addition to selecting one of the gear variants in terms of transmission forces and transmission ratios, it is possible, as has been mentioned, also to vary the initial return path Z of the sleeve tube 14 and to adapt it to the respective stent diameter and braid angle. This also permits irrational numbers as total transmission ratios $(Z+X)/Y \geqq 0.5$ ("greater than or equal to") between the return path of the sleeve tube 14 and the forward movement of the pushing element 20.

What is claimed is:

1. A device for inserting a self-expanding stent into a body vessel, the device comprising:
   a tube which, in a distal portion, keeps the stent radially compressed,
   a pushing element, which is guided in the tube and has a proximal end and a distal end,
   a grip having a housing via which the pushing element is secured displaceably on the grip,
   a stent carrier which is guided in the pushing element and has a tip which is mounted fixedly on the device via the grip,
   wherein a movable element is guided in the housing of the grip and is coupled to the proximal end of the pushing element via a cable pulley provided in the grip in such a way that, by a movement of the movable element in the proximal direction, the pushing element is at the same time pulled in the distal direction, and the tube in the proximal direction, and wherein a pull grip is also provided in the housing and is coupled to the tube, and wherein the cable pulley has a first tensioning thread which is secured with a first end of the first tensioning thread on the movable element, wherein the first tensioning thread is further guided to the pushing element via a first deflection element provided on the distal end of the housing and wherein the first tensioning thread is secured with a second end of the first tensioning thread on the pushing element.

2. The device as claimed in claim 1, wherein the device further comprises a second deflecting element which works as an opposing deflecting element of the cable pulley.

3. The device as claimed in claim 1, wherein the grip further comprises a gripping element mounted fixedly on the housing.

4. The device as claimed in claim 1, wherein the starting distance between the pulling grip and the movable element is $\geqq 0$ mm.

5. The device as claimed in claim 1, wherein it further comprises a stop element which is displaceable between the movable element and the pushing element, and configured to prevent direct abutment of the movable element with the proximal end of the pushing element.

6. The device as claimed in claim 1, wherein the first tensioning thread being secured with its second end on the pushing element comprises securing the first thread to a hook element.

7. The device as claimed in claim 1, wherein the first deflecting element comprises a gear.

8. The device as claimed in claim 2, wherein the second deflecting element comprises a gear.

9. The device as claimed in claim 2, wherein the second deflecting element is mechanically coupled to a proximal area of the housing of the grip.

10. The device as claimed in claim 1, further comprising a second tensioning thread wherein at least one end of the second tensioning thread is secured on the movable element.

11. The device as claimed in claim 1, further comprising a second tensioning thread wherein at least one end of the second tensioning thread is secured to the pushing element.

12. The device as claimed in claim 2, further comprising a second tensioning thread wherein the second tensioning thread is guided via the second deflection element.

13. The device as claimed in claim 2, further comprising a second tensioning thread, wherein at least one end of the second tensioning thread is secured on the movable element, at least one end of the second tensioning thread is secured to the pushing element, and wherein the second tensioning thread is guided via the second deflection element.

14. The device as claimed in claim 13, wherein the second tensioning thread being secured with at least one end on the pushing element comprises securing the second thread to a hook element.

15. The device as claimed in claim 13, wherein the second tensioning thread being secured with at least one end on the movable element comprises securing the second thread to a hook element.

* * * * *